(12) United States Patent
Escano

(10) Patent No.: US 6,808,534 B1
(45) Date of Patent: Oct. 26, 2004

(54) COLLAPSIBLE JACKET GUARD

(75) Inventor: Arnold M. Escano, Santa Clara, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 65 days.

(21) Appl. No.: 10/023,027

(22) Filed: Dec. 17, 2001

Related U.S. Application Data

(63) Continuation-in-part of application No. 09/505,598, filed on Feb. 16, 2000.

(51) Int. Cl.[7] .................................................. A61F 2/06
(52) U.S. Cl. .................... 623/1.23; 623/1.11; 623/1.13; 623/1.35; 604/96.01; 606/108
(58) Field of Search ....................... 604/96.01; 606/108; 623/1.11, 1.13, 1.23, 1.35, 1.36

(56) References Cited

U.S. PATENT DOCUMENTS

| 5,201,757 A | 4/1993 | Heyn et al. | |
| 5,275,622 A | 1/1994 | Lazarus et al. | |
| 5,445,646 A | 8/1995 | Euteneuer et al. | |
| 5,484,444 A | 1/1996 | Braunschweiler et al. | |
| 5,534,007 A | 7/1996 | St. Germain et al. | |
| 5,545,209 A | 8/1996 | Roberts et al. | |
| 5,693,086 A | * 12/1997 | Goicoechea et al. | ........ 623/1.11 |
| 5,713,917 A | * 2/1998 | Leonhard et al. | ............ 606/194 |
| 5,728,068 A | * 3/1998 | Leone et al. | ................. 604/101 |
| 5,755,777 A | 5/1998 | Chuter | |
| 5,902,333 A | 5/1999 | Roberts et al. | |
| 5,902,334 A | 5/1999 | Dwyer et al. | |
| 6,102,940 A | * 8/2000 | Robichon et al. | ........... 623/1.11 |
| 6,511,503 B1 | * 1/2003 | Burkett et al. | .............. 623/1.11 |

* cited by examiner

Primary Examiner—David H. Willse
Assistant Examiner—Javier G. Blanco
(74) Attorney, Agent, or Firm—Fulwider Patton Lee & Utecht, LLP

(57) ABSTRACT

An improved reduced diameter intraluminal grafting system capable of deploying a bifurcated graft into a bifurcated vessel is described. The system having a pliable jacket guard configured to ensure atraumatic delivery and deployment of the bifurcated graft. The bifurcated graft is comprised of a main tubular member and two tubular legs with attachment systems configured into each of the three ends of the graft. The bifurcated graft along with the mechanisms required to position and attach the bifurcated graft fit within a single delivery catheter for intraluminal delivery. The bifurcated graft, positioning mechanisms and attaching mechanisms are configured such that a small diameter delivery catheter can be utilized. The methods of positioning and attaching the bifurcated graft are also described.

25 Claims, 12 Drawing Sheets

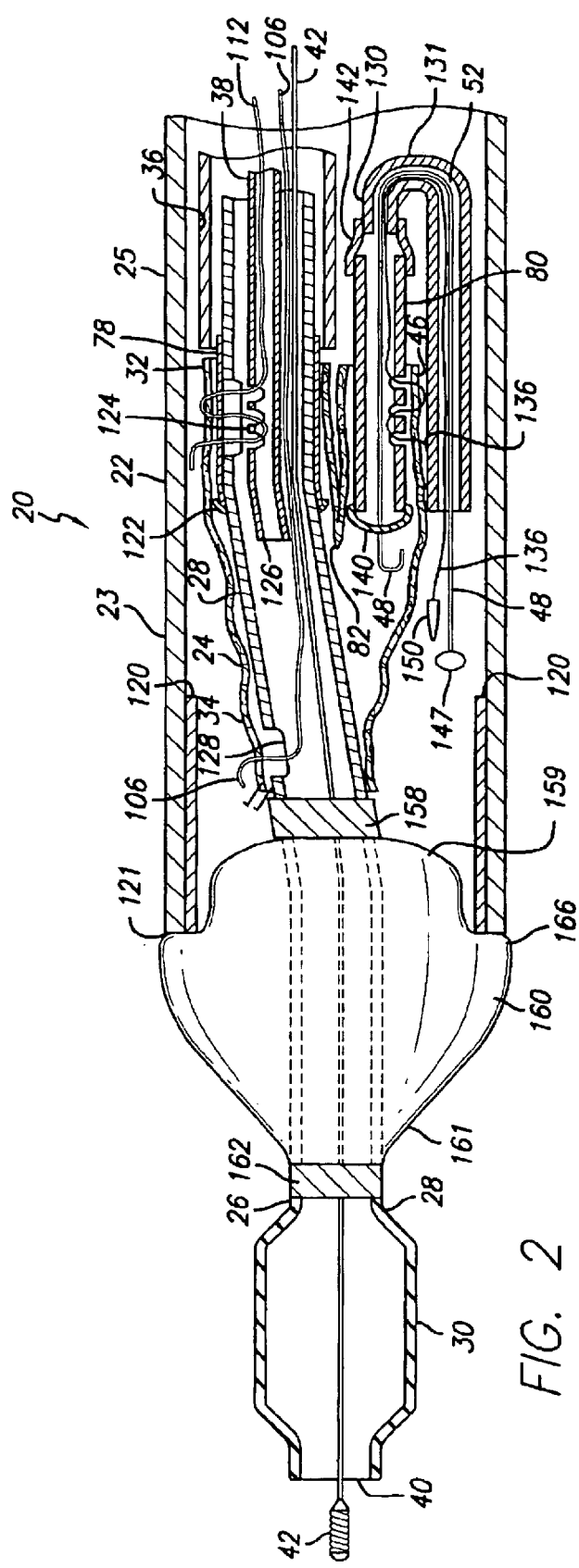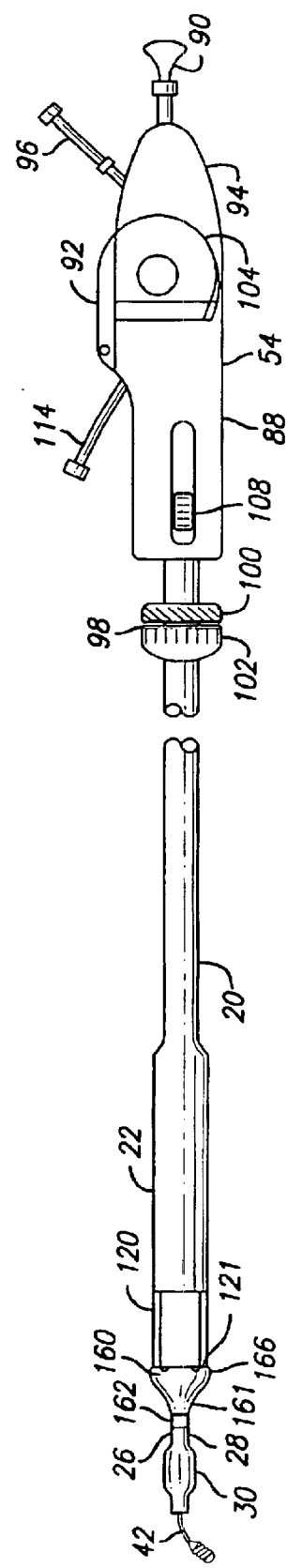

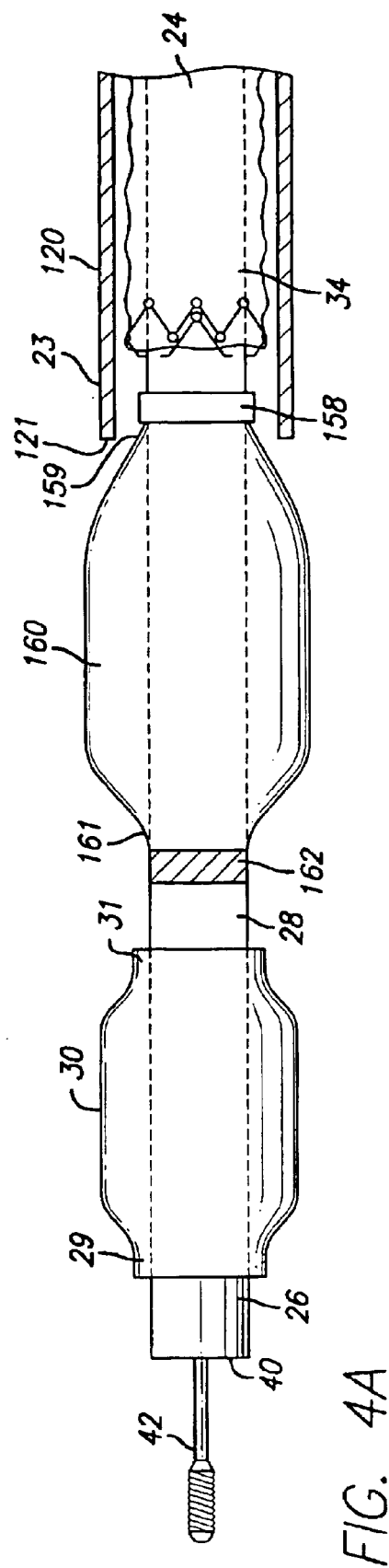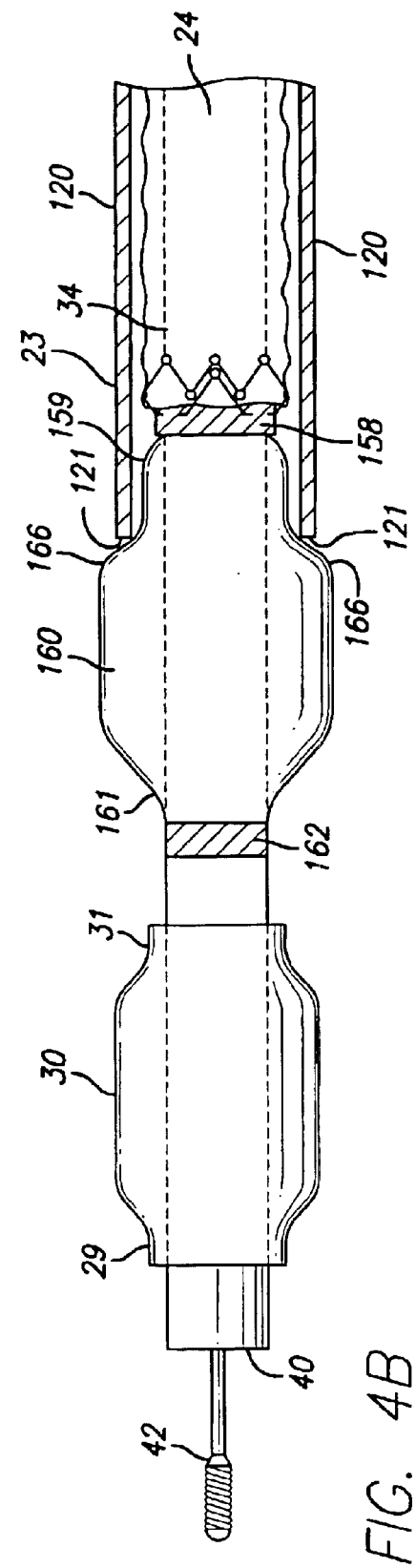

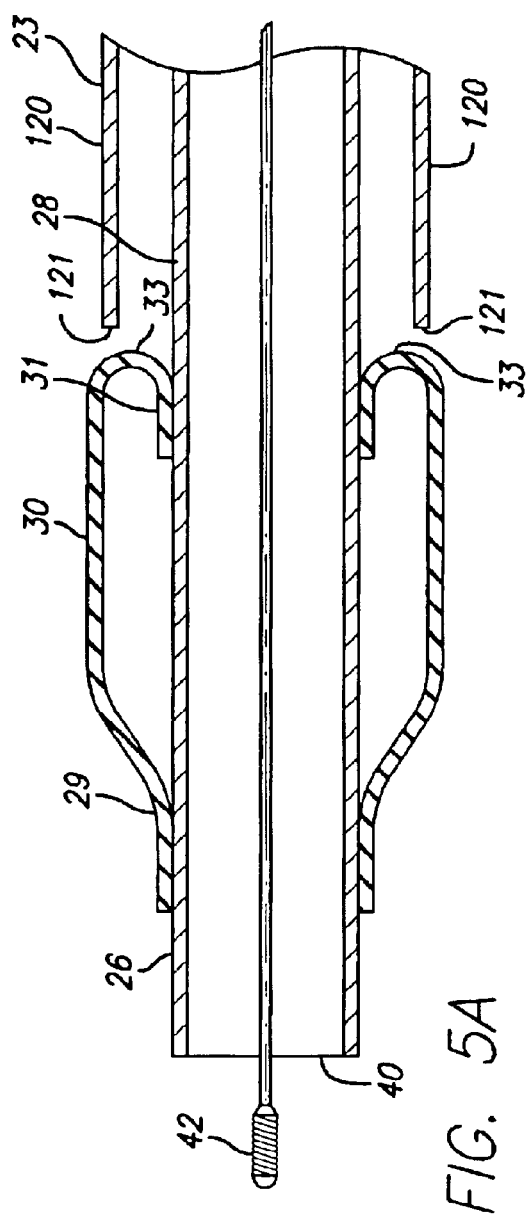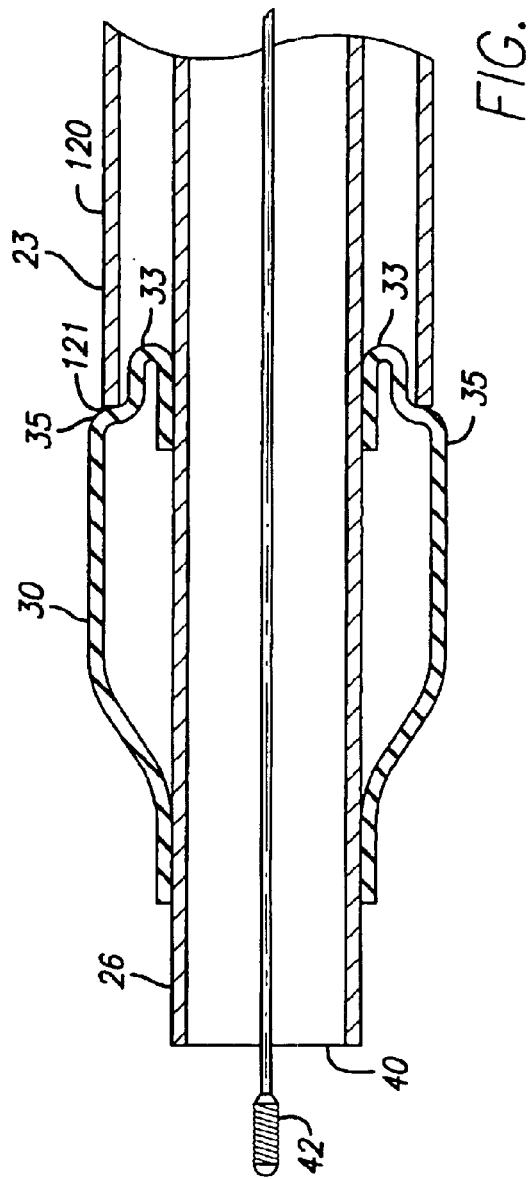

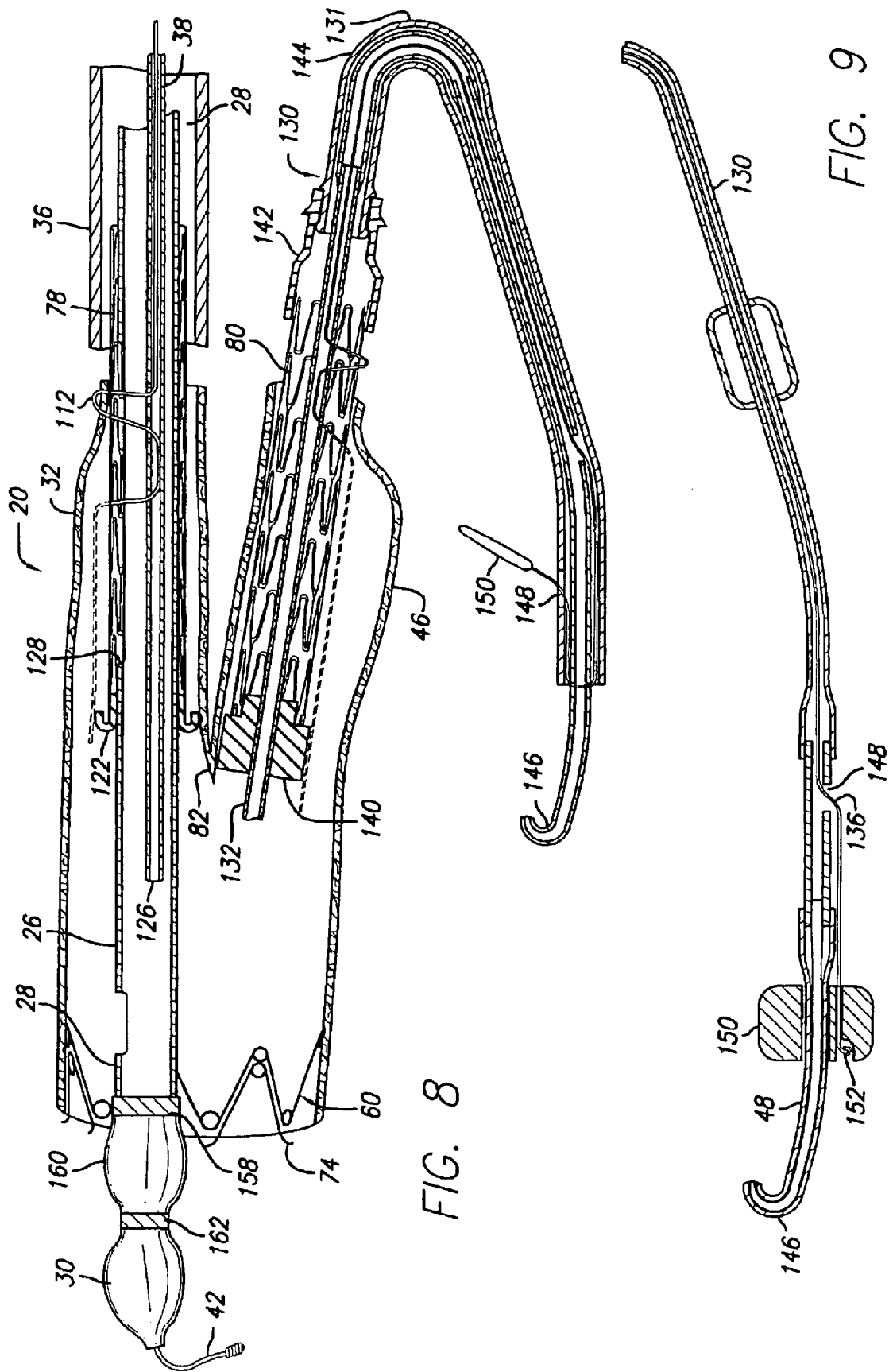

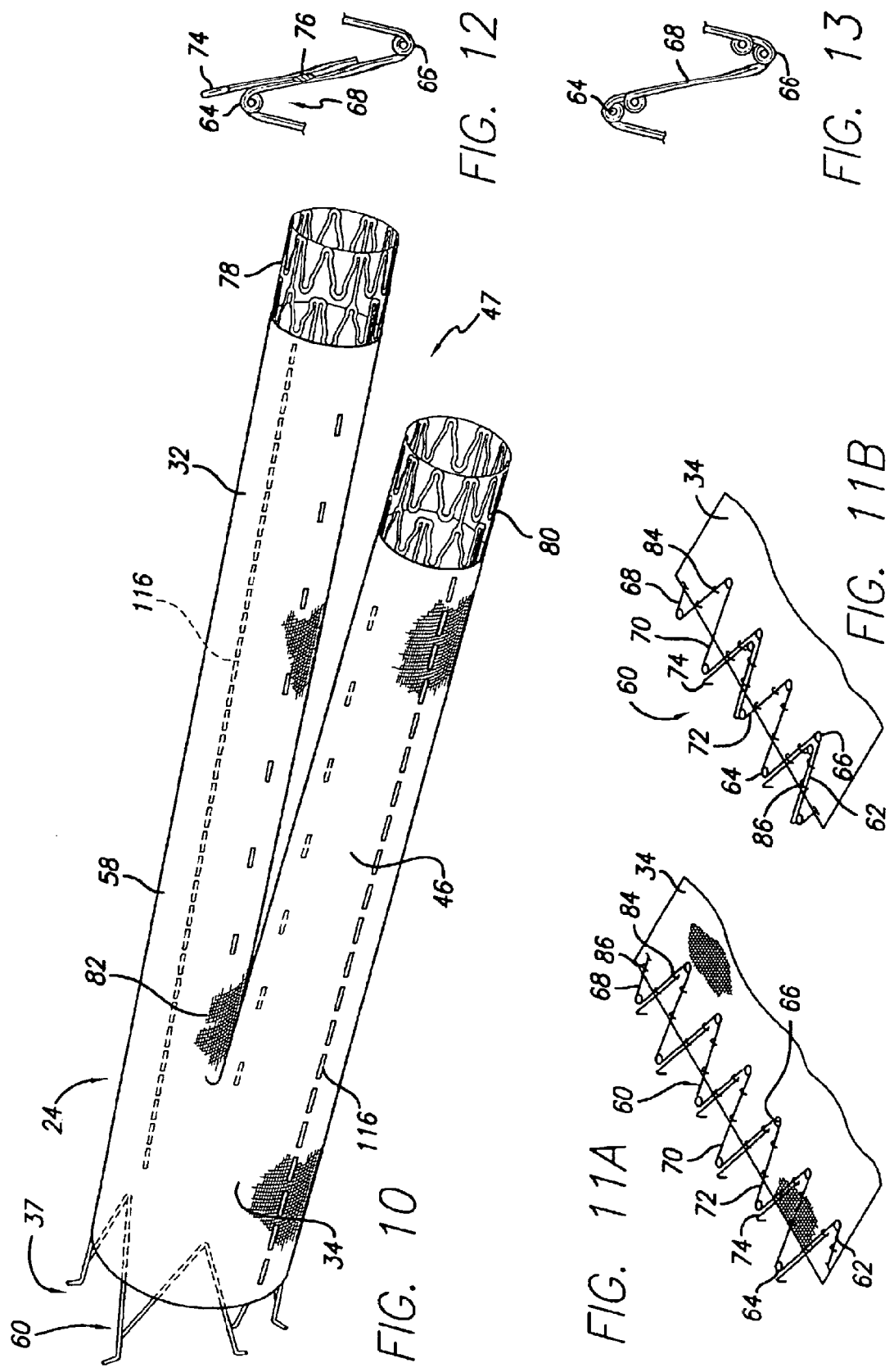

COLLAPSIBLE JACKET GUARD

CROSS-REFERENCES TO RELATED APPLICATIONS

This application is a continuation-in-part of application Ser. No. 09/505,598, filed Feb. 16, 2000. The contents of that application are hereby incorporated herein by reference.

BACKGROUND OF THE INVENTION

This invention relates to a system and method for emplacing a prosthesis and more particularly, to a reduced profile delivery system and method of use for placement of a bifurcated graft having attachment systems within a corporeal lumen.

It is well established that various fluid conducting bodies or corporeal lumens, such as veins and arteries, may deteriorate or suffer trauma so that repair is necessary. For example, various types of aneurysms or other deteriorative diseases may affect the ability of the lumen to conduct fluids and in turn may be life-threatening. In some cases, the damaged lumen is repairable only with the use of a prosthesis such as an artificial vessel or graft.

For repair of vital vessels, such as the aorta, surgical repair is significantly life-threatening. Surgical techniques known in the art involve major surgery in which a graft resembling the natural vessel is spliced into the diseased or obstructed section of the natural vessel. Known procedures include surgically bypassing the damaged or diseased portion of the vessel and inserting an artificial or donor graft attached to the native vessel by an anastomosis.

It is known within the art to provide a prosthesis for intraluminal repair of a vessel, such as an abdominal aorta having an aneurysm. The art has taught to provide a prosthesis positioned in a vessel and then to secure the prosthesis within the vessel with hooks or staples. Improvements since the earliest prosthesis and intraluminal delivery systems have attempted to increase the flexibility of the entire grafting system and reduce the complexity of the implantation procedure.

More recent art has taught the use of bifurcated grafts having attachment systems configured on each end of the graft prior to delivery. These attachment systems required the use of multiple balloon catheters to expand each of the attachment systems individually. Although these recent improvements simplify the procedure and reduce risks to the patient, more improvement is possible.

In recent years, several devices have been developed in an attempt to treat an aortic aneurysm through intraluminal repair. For example, a method and article for performing an aneurysm repair, wherein a prosthetic graft is utilized to replace the damaged segment of the blood vessel have previously been developed. A plurality of radially spaced anchoring pins are located adjacent each end of the graft and provide means for securing the graft to the wall of the vessel. An assembly is provided for moving the graft within the vessel and permanently anchoring the graft to the wall of the vessel.

Additionally, there has been previously described a bifurcated aortic graft constructed for intraluminal insertion having a plurality of struts having angled hooks with barbs at their superior ends. An assembly for inserting the graft and implanting the hooks into the vessel lumen is also disclosed.

Others have disclosed an intraluminal grafting system including a hollow graft having an attachment means located at one end of the graft. The system includes positioning means for moving the graft within the vessel, the positioning means having a capsule positioned at one end for covering the graft attachment means. The disclosed positioning means further includes an inflatable member for securing the attachment means within the lumen.

Moreover, there has been described an aortic graft and apparatus for repairing an aneurysm that includes a tube graft secured within the aorta and an attachment means at each end of the graft. Intraluminal delivery is accomplished using a catheter having a balloon for expanding and securing the attachment means. The graft and attachment means are preferably enclosed by a sheath which covers the entire graft and attachment means.

There have also previously been developed arrangements including an intraluminal grafting system including a tubular graft having attachment means positioned at both ends. The system includes a positioning means for transporting the graft through a vessel lumen and for deploying the graft within the lumen. The positioning means includes an inflatable member, a capsule and means for removing the graft from the capsule. The capsule is disclosed as a rigid cylindrical member covering the entire graft.

A sheath for use in introducing a catheter in the body of a patient has also been previously described. The sheath includes a flexible elongate tube and a backflow adapter having a hemostatic valve secured to the proximal extremity of the tube. The sheath may be used for introducing a deployment catheter into a femoral artery of the patient. The use of a sheath in such a manner has proven to be beneficial in the delivery and deployment of a graft prosthesis, however, several drawbacks must still be addressed. For example the leading edge of the sheath may cause trauma to the vessel during delivery. One attempt to remedy this problem was introduced in the form of a rigid guard member positioned upon the distal portions of the delivery system that may provide a covering and a smooth transitional surface about the leading edge of sheath thereby buffering the traumatic leading edge from causing damage to the vessel during the delivery of the graft prosthesis. However, this attempted solution has been shown to be of limited benefit as the rigid guard member may cause further complications during the deployment process such as snagging a partially deployed graft during the deployment procedure. Therefore, further improvements may be made to enhance the safety and ease of use of such a system.

To provide consistency with the common usage of terms used in the medical surgical arts in the United States, the terms "proximal, distal, inferior and superior" are used with a certain regularity within the present specification. "Proximal" refers to parts of the system, such as catheters, capsules and wires, which are closest to the user and closest to that portion of the system lying outside or exterior of the patient. "Distal" refers to the point farthest from the user and typically most interior of the corporeal lumen. The term "superior" refers to a location situated upstream of the flow of blood and is used herein in description of the graft and attachment system. "Inferior" refers to the point situated downstream of the flow of blood and again is used herein with reference to the graft and attachment system.

A typical procedure used with the described invention uses a "femoral approach." This term describes an application which begins with an incision in the femoral artery. Similarly, the described invention may be used in an "iliac approach" which begins with an incision in the iliac artery. Using the terminology defined in the previous paragraph, the distal tip of the system maybe inserted into the femoral artery and advanced upstream into the iliac artery and the abdominal aorta. Thus, the more distal portions of the system reside upstream of those portions described as more proximal. Furthermore, in the described procedure, the superior portions of the graft will permanently reside in the abdominal aorta, while the inferior portions will reside in the iliac arteries.

The terms "ipsilateral" and "contralateral" typically refer to opposing portions of a corporeal lumen having symmetric right and left sides. "Ipsilateral" refers to those portions residing on the same side through which the grafting system enters the corporeal lumen, while "contralateral" refers to the opposite portions. Therefore, this distinction is dependent on whichever side (right or left) the physician decides to insert the grafting system. The portions of the grafting system which reside or operate within the symmetric vessels of the corporeal lumen use the same terminology. For example, the physician may insert the grafting device into the ipsilateral femoral artery, advance the device through the ipsilateral iliac artery and into the abdominal aorta. Then the device can be manipulated downstream into the contralateral iliac artery.

What has been needed and heretofore unavailable is an improved delivery system that will provide for the atraumatic delivery of a graft prosthesis within the patients vasculature, will not cause further complications during the deployment of the graft prosthesis, and will be fairly easy to use and manipulate by an operating physician. The present invention as described herein fulfills these and other needs.

SUMMARY OF THE INVENTION

Briefly and in general terms, the present invention is directed towards repairing vasculature. More particularly, the present invention includes a system that is configured to accomplish intraluminal repair of defects such as aneurysms found in blood vessels.

In one aspect, the system of the present invention includes a catheter for intraluminally delivering an endovascular device at a target site within vasculature.

In one embodiment, the catheter includes a jacket guard configured to provide the system with an enhanced atraumatic profile.

In other aspects, the present invention embodies an intraluminal delivery system for securing a prosthesis within the vessels of the corporeal lumen of an animal, such as a human. The preferred embodiment of a placement system is configured for introducing a graft into a corporeal lumen and positioning the graft in the area of the aortic bifurcation. The delivery system embodies a main catheter capable of containing the prosthesis and placement system for intraluminal delivery. A significant improvement of this system is the use of a main catheter having a smaller diameter from the prior art systems. Another significant improvement is the introduction of a pliable jacket guard located slightly proximal to an expandable member on the main catheter for assisting in the smooth delivery and deployment of a graft prosthesis. The jacket guard which may embody various different forms protects the vessel during delivery of the system by providing a buffer against trauma.

In general, the present invention provides an intraluminal grafting system and method which improves upon the prior art systems. One feature that impacts the capability of any intraluminal device or delivery system is the size of the system's components. Reducing the size of the components, and ultimately the total delivery system, allows accessing smaller arteries without injury to the artery as well as increasing flexibility. The challenges associated with reducing the size of the system have been met by the present invention. The mechanisms of the present invention have been arranged to fit within a smaller circumferential area than what was capable with prior art devices. Furthermore, the procedures associated with the present invention have been modified to reflect the novel arrangement of the mechanisms. This allows the use of a small diameter delivery catheter having diameter significantly smaller than what is taught in the prior art. The present invention comprises a system and method for implanting a prosthesis utilizing such a small diameter delivery catheter. The small diameter delivery catheter is designed for traversing the femoral, iliac and aortic vessels of a human anatomy.

The present invention also provides an intraluminal grafting system having a pliable jacket guard. Along with the reduced size of the present invention, the pliable jacket guard provides improved safety and accessability to smaller arteries. The jacket guard provides for atraumatic navigation during delivery by embodying a relatively soft leading edge. Furthermore, once the system is properly positioned within a target vessel, the jacket guard further assists in the placement and deployment of a graft prosthesis by providing for a smoother transition between terminal ends of the graft prosthesis which must be securely anchored within the target vessel.

The present system has several advantages over prior art systems. For example, the reduced diameter delivery catheter having a pliable jacket guard causes less trauma to the femoral and iliac arteries while inserting and delivering the grafting system. In addition, the small diameter delivery catheter permits the use of the invention in a larger patient population because of the variances in iliac vessel diameters. Similarly, the smaller system having a pliable jacket guard may allow for easier navigation inside the corporeal lumen especially with more difficult anatomy by reducing the likelihood that vessel injury or trauma will result from any sharp leading edges found on delivery catheters or the like.

The simplified delivery and attachment methods provide advantages to physician and patient which are not available with prior art devices. Ease of use eliminates many of the complications involved with other devices. Shorter procedure times allowed by simplified delivery further reduces the trauma to the patient due to interruption of the flow of blood through the aorta and iliac arteries.

The prosthesis delivered by the present system comprises an inverted wye-shaped bifurcated graft having an attachment system at each of its three orifices. The upper attachment system, which is used to anchor the graft into the abdominal aorta, preferably uses a series of sharpened outwardly disposed members to engage the aorta. The upper attachment system may be balloon-expandable, self-expandable or partially both. The two lower attachment systems, which are used to implant the graft into the iliac arteries, preferably employ self-expanding attachment systems which also support the lower extremities of the graft, but may also be balloon expandable or partially both.

In the preferred embodiment, the two lower attachment systems, comprised of self-expanding attachment systems, are restrained in a compressed condition by release wires residing along side the elements of the attachment systems. These release wires are also described herein as "pull wires" which describes the method by which they release the attachment system. Once the graft is positioned correctly in the aorta and iliac arteries the release wires can be removed, allowing the attachment systems to expand. When the attachment systems are expanded the lower extremities of the graft are attached within the iliac arteries. The release wires can then be entirely removed from the patient leaving the graft securely attached within the iliac arteries.

Preferably, the self-expanding attachment systems in the lower extremities of the graft are arranged to extend superiorly near to the septum of the bifurcation and proximally below the orifice of each lower extremity. For example, the proximal end of the attachment systems may extend approximately 20 mm below the proximal end of the lower extremity. The lower extremities are thus fully supported by the attachment systems when deployed which prevents twisting and bunching of the graft. The graft is also securely attached within the iliac arteries throughout the entire length of the attachment systems. This configuration allows for greater patient activity and mobility without dislodging the graft.

The upper, or superior, member of the graft is positioned by advancing the grafting system through the patient's vascular system. The grafting system includes a metal catheter ring located at a position corresponding to the attachment system of the superior member of the graft. The metal catheter ring protects the sharp wall engaging members of the graft attachment system during delivery. First the grafting system is inserted into the patient's ipsilateral femoral artery or external iliac artery. The grafting system is then advanced through the arteries until it passes through the ipsilateral iliac artery, past the aortic bifurcation and into the aorta. The system is then advanced through the aorta until it crosses the aneurysm to be treated. A portion of the main delivery catheter having a metal catheter ring is then withdrawn relative to the remainder of the system exposing the graft. The superior member is thereby located within the aorta superior to the aneurysm.

As the main delivery catheter exposes the graft, the contralateral inferior member is exposed, as well as an attached contralateral delivery system. Preferably the contralateral delivery system includes a contralateral delivery catheter, a contralateral guidewire and a contralateral release wire fastened to the contralateral attachment system. The contralateral guidewire may include a knob or hook on its distal end. This knob or hook is configured to allow the contralateral guidewire to be snared by a wire designed for this purpose which is advanced through the contralateral femoral artery and iliac artery. Once the guidewire is snared the contralateral portion of the grafting system may be guided down into the contralateral iliac artery, and correctly positioned therein.

As the main delivery catheter exposes the graft, the proximal end of the ipsilateral inferior member remains attached within an ipsilateral delivery catheter. This ipsilateral delivery catheter is disposed throughout the main catheter and can be independently translated. It is used to pull the ipsilateral inferior member back into the ipsilateral iliac artery, and correctly position it therein.

Preferably, the delivery system includes a balloon catheter assembly capable of expanding the attachment system of the superior member of the graft. Expanding the system in this manner urges the outwardly disposed members, if present, into the wall of the aorta which is one method of securely fastening the system thereto. The balloon catheter assembly further includes a pliable jacket guard located slightly proximal to the expandable member. The jacket guard provides for a traumatic delivery of the system during placement and deployment of the attachment system of the superior member of the graft. Preferably, the balloon catheter has a multilumen catheter shaft. At least one of these lumens allows the inflation of the balloon. Others house the delivery system for the ipsilateral extremity, the release wire for the ipsilateral self-expanding attachment system, and the main guidewire. Preferably, the release wire is also housed within a small diameter cylinder which allows the balloon catheter to be advanced and retracted relative to the release wire.

The main guidewire extends distally beyond the remainder of the system. The main guidewire also extends proximally throughout the system and out of a control device such that its proximal end can be manipulated by the physician. In this manner the main guidewire may be advanced to a desired location and aid in the manipulation of the remainder of the system. Such a guidewire may be of a configuration typical to prior art procedures, or may be specifically designed for use in a reduced diameter delivery system.

The ipsilateral lower extremity of the graft is deployed into the ipsilateral iliac artery by retracting the ipsilateral release wire. The physician has independent control of the ipsilateral release wire which may be pulled proximally with respect to the remainder of the system. By pulling the ipsilateral release wire proximally it is unfastened from the members of the ipsilateral attachment system and the ipsilateral lower extremity. This allows the ipsilateral attachment system to expand toward the wall of the artery. The ipsilateral release wire and cylinder may then be removed from the patient and the system.

Optionally, once the ipsilateral attachment of the ipsilateral lower extremity is expanded, further securing of the attachment system may be accomplished by positioning the expandable member of the balloon catheter over the expanded ipsilateral attachment system and expanding the expandable member to further expand and engage the ipsilateral attachment system into the vessel wall. This optional procedure is assisted by the pliable jacket guard located slightly proximal of the expandable member. During the positioning of the balloon catheter over the ipsilateral attachment system, the balloon catheter is moved proximally within the partially deployed graft device. This proximal movement of the balloon catheter may cause the partially deployed graft to be buckled or snagged thereby resulting in either dislodgement of the partially deployed graft or at the least, trauma to the vessel wall.

Beneficially, the pliable jacket guard of the present invention reduces the likelihood that the balloon catheter may snag on the graft walls by providing a soft smooth transitional edge surface at the proximal end of the jacket guard. Therefore, it will be appreciated that the jacket guard will improve the safety as well as assist in the delivery of the graft system and the deployment of the graft attachment systems both the superior attachment system and the ipsilateral attachment system.

Once the contralateral lower extremity is correctly positioned into the contralateral iliac artery, it may be deployed in much the same way as the ipsilateral lower extremity. The contralateral positioning system has various possible configurations. All of the configurations allow for the contralateral release wire to be pulled proximally with respect to the remainder of the system and unfastened from the contralateral extremity and contralateral attachment system. Once the contralateral release wire is withdrawn and the contralateral attachment system deployed, the remainder of the contralateral system may be removed from the patient and the system.

The remaining components of the system may be withdrawn from the patient at any time the components are free from the others. This leaves the graft in place and secured across the aortic bifurcation. The bifurcated graft safely maintains the blood flow throughout the region. Once the delivery system components are removed from the body, the access to the corporeal lumens may be closed.

Other features and advantages of the present invention will become apparent from the following detailed description, taken in conjunction with the accompanying drawings, which illustrate by way of example, the principles of the invention.

BRIEF DESCRIPTION OF THE DRAWINGS

FIG. 2 is an enlarged partial cross-sectional view, depicting the present invention jacket guard located at a distal end of the delivery system configured for intraluminal delivery;

FIG. 3 is a plan view, depicting the delivery system;

FIG. 4A is an enlarged partial cross-sectional view, depicting a first embodiment of the present invention jacket guard;

FIG. 4B is an enlarged partial cross-sectional view, depicting a delivery catheter as used in conjunction with the embodiment of FIG. 4A;

FIG. 5A is an enlarged cross-sectional view, depicting a second embodiment of the present invention wherein the expandable member is configured for use as a jacket guard;

is FIG. 5B is an enlarged partial cross-sectional plan view, depicting a delivery catheter as used in conjunction with the embodiment of FIG. 5A;

FIG. 8 is an enlarged partial cross-sectional plan view, depicting a third embodiment of the grafting system with the bifurcated graft partially deployed;

FIG. 9 is an enlarged partial cross-sectional plan view, depicting one embodiment of the components of the grafting system used to deploy the contralateral tubular leg of the bifurcated graft;

FIG. 10 is a perspective view, depicting the bifurcated graft with the attachment systems deployed;

FIG. 11A is a perspective view, depicting a first embodiment of the superior end of the bifurcated graft as it would appear if unrolled;

FIG. 11B is a perspective view, depicting a second embodiment of the superior end of the bifurcated graft as it would appear if unrolled;

FIG. 12 is an enlarged plan view, depicting the apices and wall-engaging member of the superior attachment system of the embodiment of FIG. 11A;

FIG. 13 is an enlarged plan view, depicting the apices of another embodiment of the superior attachment system of the bifurcated graft;

DETAILED DESCRIPTION OF THE PREFERRED EMBODIMENTS

Figure 1:
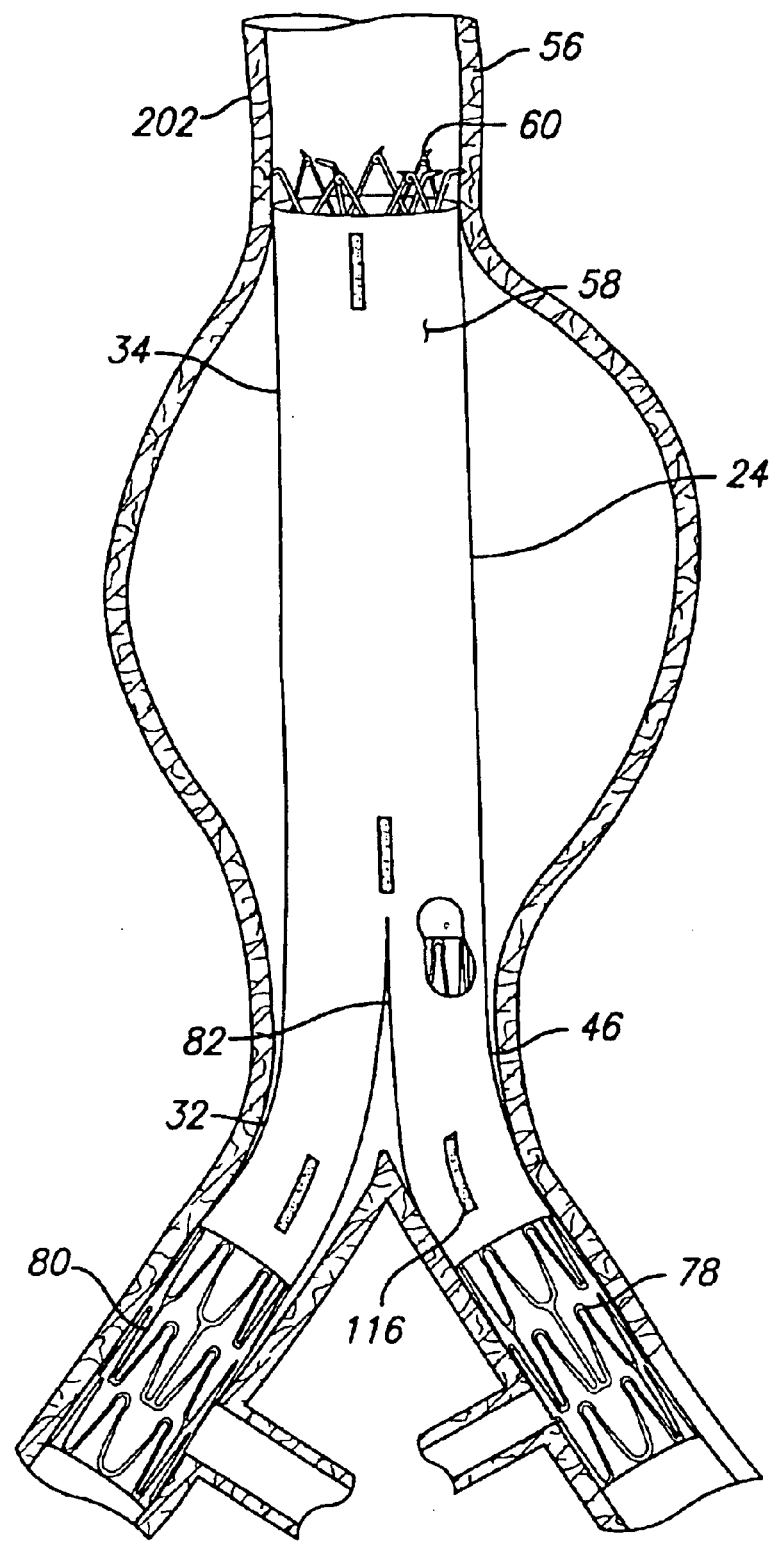
FIG. 1 is a partial cross-sectional view, depicting a bifurcated graft implanted in the aortic bifurcation of a human.

As shown in the drawings and for purposes of illustration the invention is embodied in an intraluminal delivery system 20 for a bifurcated graft 24. The major components of the system include the bifurcated graft, a main catheter assembly 22, a balloon catheter assembly 26 having a jacket guard 160, and a control assembly 54. The delivery system 20 includes several components particular to the placement of the graft across a vascular bifurcation such as the aortic bifurcation. One of the features of the invention is the use of a main delivery catheter 23 having a diameter smaller than what has been achieved in prior art systems. Most of the components for the delivery and placement of the graft are delivered together within this reduced-diameter delivery catheter. Additionally, the system includes a balloon catheter assembly 26 having a shaft 28, an expandable member 30 and a jacket guard 160. The jacket guard 160 is used to buffer and protect the vessel walls from the leading edge of the main delivery catheter 23 during delivery of the system within the vasculature and also during retraction of the system after deployment. The jacket guard 160 also serves other functions necessary to the deployment of the bifurcated graft, as will be described further below. Furthermore, the system includes various features which allow it to be delivered within the reduced diameter of the delivery catheter. These features include providing simplified delivery mechanisms for both the ipsilateral and contralateral inferior legs of the prosthesis. Additional features include simplified mechanisms for attaching the graft limbs and increased flexibility of the entire system.

In the present system, the graft 24 is comprised of a bifurcated tubular prosthesis having superior and inferior extremities. The superior member 34 of the graft comprises a main tubular member which bifurcates into two tubular legs 32 and 46 which comprise the inferior extremities of the graft. For clarity, the two tubular legs are referred to as the ipsilateral inferior member 32 and the contralateral inferior member 46. An attachment system 60 is secured to the superior end of the main tubular member 34 as well as to the inferior ends of each of the tubular legs 32 and 46. The superior attachment system 60 secured to the superior member may be provided with wall-engaging members 74 which are retracted during delivery. A balloon catheter assembly 26 having a jacket guard 160 is included for expansion of the superior attachment system. The superior attachment system may also be self-expanding. The attachment system 78 and 80 of each inferior tubular member includes a self-expanding attachment system which is compressed during delivery. Release wires 106, 112, and 136 keep the attachment systems in a compressed condition until the bifurcated graft 24 is appropriately positioned. The attachment systems are expanded by pulling the release wires out of the attachment systems. Due to the integrated nature of the inferior members and these attachment systems, the references herein to the inferior tubular members may include the attachment systems, or where appropriate, the attachment system may be referenced separately.

Much of the terminology used herein is variable. Those skilled in the art will recognize many of the components described herein by other terms. For example, the parts of the bifurcated graft may be referred to as superior and inferior members as well as upstream and downstream ducts or as distal and proximal extremities. The attachment systems are also referred to as expandable anchors which is descriptive of how the systems operate. The delivery components include tubular devices known as catheters in many different configurations. There exists a main delivery catheter for delivery of the entire system as well as secondary catheters which are used within the ipsilateral and contralateral blood vessels. The use of particular terminology herein is not intended as a limitation, rather terminology is intended to encompass the varied references known to those of skill in the art.

In more detail, the intraluminal grafting system 20 is shown in FIGS. 2–9. As shown in FIG. 2 the system includes a main catheter assembly 22, a bifurcated graft 24, and a balloon catheter assembly 26. The balloon catheter assembly 26 embodies a balloon catheter shaft 28, an expandable balloon member 30, and a jacket guard 160. The balloon catheter shaft 28 is disposed within the main delivery catheter 23 with the expandable balloon member 30 and the jacket guard 160 extending distally.

Referring to FIG. 4A, a first embodiment of the jacket guard 160 includes a distal end 161 and a proximal end 159. The jacket guard distal end 161 may be securely attached at a fixed attachment point 162, by any known form of adhesion, such as being fused to the distal extremity of the balloon catheter assembly. The attachment point 162 may be located at a position slightly proximal of the expandable balloon member 30. The jacket guard proximal end 159 is connected to a circular ring 158, the ring being positioned and disposed about the balloon catheter shaft 28 and is capable of lateral motion about a longitudinal axis of the balloon catheter shaft. The jacket guard 160 may be constructed of any pliable biocompatible material and has the property of having an expanded profile while in a compressed or collapsed mode and a smaller or lower profile in an relaxed mode.

Referring to FIG. 4B, the jacket guard 160 serves the function of protecting the vessel during the delivery and positioning of the system 20 and during deployment of the bifurcated graft 24. During delivery of the system, the main delivery catheter 23 may be positioned such that the a leading edge 121 of the main delivery catheter butts up against and engages the jacket guard thereby collapsing the jacket guard 160 and producing a larger profile having an outer diameter greater than the outer diameter of the main delivery catheter. Because the jacket guard 160, in a compressed condition has a larger profile than the outer diameter of the main delivery catheter 23, an overlap 166 is formed near the proximal end 159 of the jacket guard. The overlap 166 encompasses the leading edge 121 of the main delivery catheter, i.e., the leading edge is tucked snugly under the overlap, thereby protecting the vessel walls from any trauma which may result from contact between the main catheter leading edge and the vessel wall during delivery.

Referring to FIG. 5A, a second embodiment of the jacket guard is depicted wherein the expandable member 30 may be configured to serve as a protective jacket guard serving a similar function as the jacket guard embodiment described above. The expandable member 30 includes a proximal end 31 and a distal end 29. The expandable member 30 is configured such that the proximal end 31 of the expandable member is attached to the balloon catheter shaft 28 in an inverted manner providing a pliable round edge 33. To achieve this configuration, during the manufacturing of the balloon catheter assembly 26, the proximal end 31 of an expandable member 30 turned inside out is attached to the balloon catheter shaft 28 and then the expandable member is inverted again and the distal end 29 is attached as usual to the balloon catheter shaft 28 at a position distal to the attachment point of the expandable member proximal end 31. This inverting or turning inside-out produces the balloon round edge 33.

Referring to FIG. 5B, similar to the first embodiment of the jacket guard (FIG. 4B), the balloon round edge 33 serves the to protect the vessel during the delivery and positioning of the system 20. During delivery of the system, the expandable member may be partially inflated providing a circumferential profile slightly larger than the outer diameter of the main delivery catheter 23. The leading edge 121 of the main delivery catheter 23 may be positioned such that it butts up against and engages the balloon round edge 33 of the partially inflated expandable member such that a portion of the balloon round edge is tucked within the main delivery catheter. As the partially inflated expandable member is partially tucked into the main delivery catheter 23, the distal portion of the expandable member 30 expands such that an overlapping region 35 results. The overlapping region 35 overlaps and encompasses the leading edge 121 of the main delivery catheter and provides protection to the vessel walls from any trauma which may result from contact between the main catheter leading edge 121 and the vessel wall during delivery.

Referring again to FIG. 2, the bifurcated graft 24 is shown collapsed within the main delivery catheter 23. The ipsilateral inferior member 32 and superior member 34 of the bifurcated graft 24 are disposed about the balloon catheter shaft 28. An ipsilateral delivery catheter 36 may also be disposed about the balloon catheter shaft 28 and at least the proximal end of the ipsilateral inferior member 32. A first cylinder 38 is also included within a first balloon catheter lumen 40. By way of example, the cylinder may be a hypotube. A main guidewire 42 may also be disposed within a second balloon catheter lumen (not shown).

Figure 6:
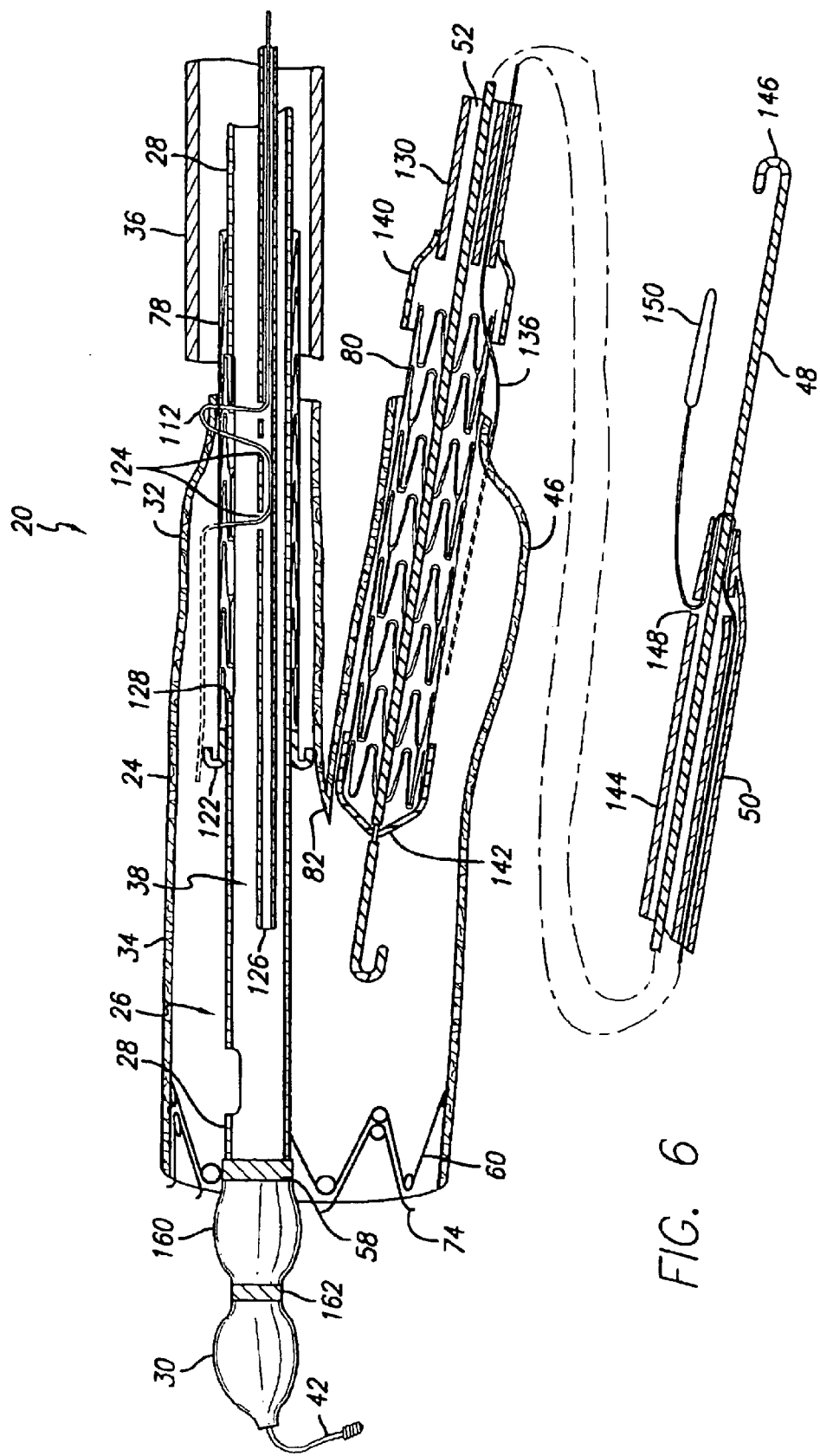
FIG. 6 is an enlarged partial cross-sectional plan view, depicting a first embodiment of the grafting system with the bifurcated graft partially deployed.
Figure 7:
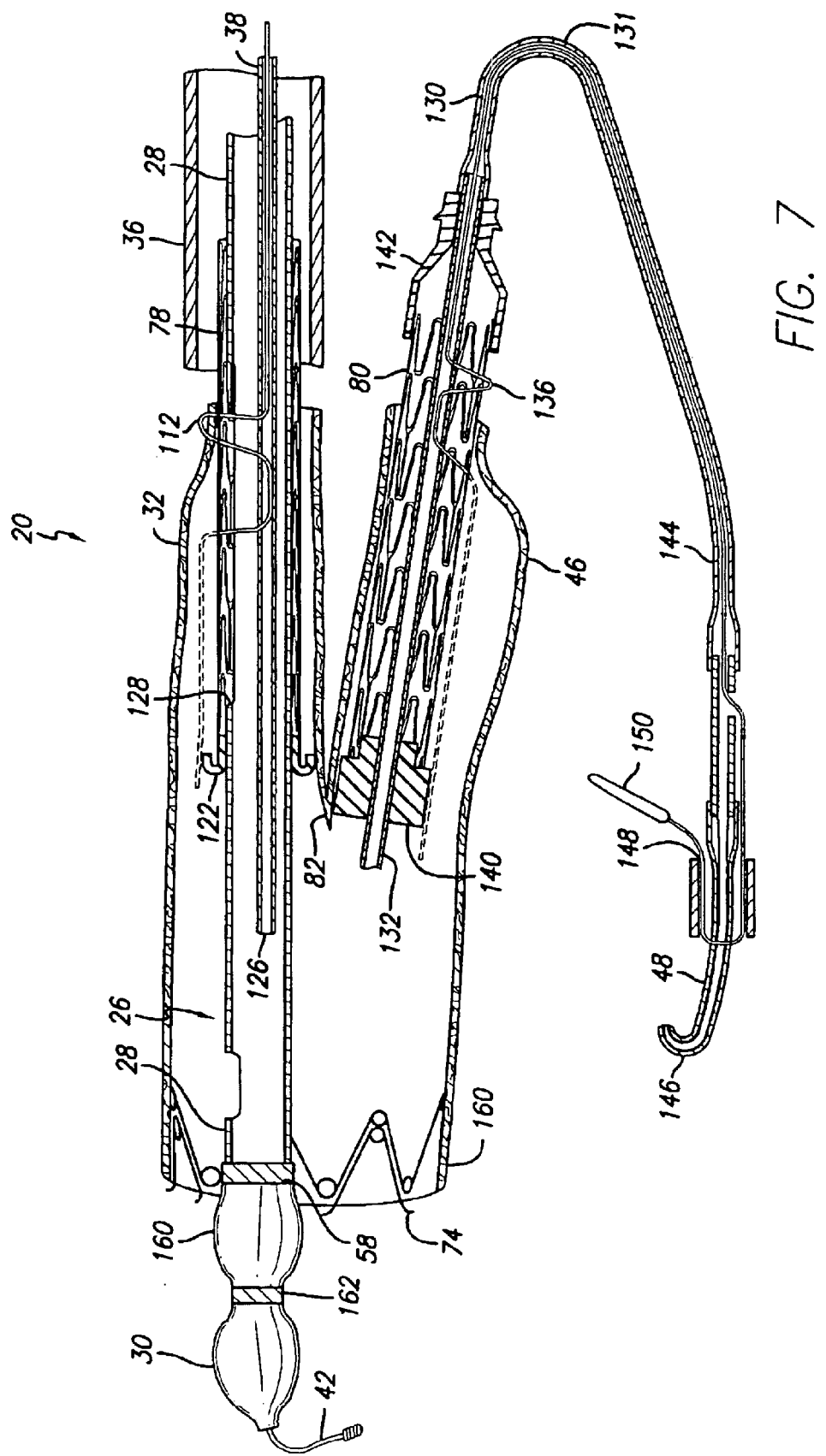
FIG. 7 is an enlarged partial cross-sectional plan view, depicting a second embodiment of the grafting system with the bifurcated graft partially deployed.

Several different embodiments of the present invention are described herein. FIGS. 6, 7 and 8 each depict one possible embodiment of this invention. The differences between these embodiments are primarily within the components for the positioning of the contralateral inferior member 46. Although a contralateral delivery catheter 130 is present in each embodiment, it has several possible configurations.

The contralateral inferior member 46 of the graft is disposed about a contralateral guidewire 48. The contralateral guidewire 48 may be formed as a stiffened wire or as a coiled wire. The proximal end of the contralateral inferior member 46 is attached to a contralateral delivery catheter 130. The contralateral guidewire 48 extends proximally through a first contralateral lumen 52. The contralateral delivery catheter 130 may include a substantial bend 131 (FIG. 2) so that the assembly may fit within the main delivery catheter 22. This bend 131 may occur midway through the length of the contralateral delivery catheter 130 and be comprised of any one of several types of flexible joints known in the art.

Those skilled in the art will appreciate that many of these components, which herein are described as parts of a graft delivery system, are also parts of related systems. For instance, the balloon catheter assembly 26, is part of a system which provides for the inflation, deflation, advancement and retraction of the balloon catheter 28. This balloon catheter system includes components on a control assembly 54 (FIG. 3) which is manipulated by the physician and remains outside of the patients vasculature. Similarly, the main guidewire 42 described as part of this invention is also part of a system designed for control of the guidewire. It should be appreciated that the details of these related systems may vary, or in fact be improved over time, without removing a device from the scope of this invention.

As shown in FIGS. 1 and 10–13 the intraluminal grafting system 20 also includes an expandable, collapsible and flexible intraluminal vascular bifurcated prosthesis or bifurcated graft 24 for implanting in a body vessel or corporeal lumen 56. Referring to FIG. 10, the graft consists of a deformable main tubular member 34 which bifurcates into an ipsilateral tubular member 32 and a contralateral tubular member 46. The main tubular member 34 and inferior tubular members 32, 46 each are formed of a graft wall 58 allowing fluid communication between the superior 37 and inferior 47 ends of the bifurcated graft 24.

The main tubular member 34 may have a length in the range of two (2) to ten (10) centimeters, where 7.5 centimeters is suitable for most patients. The main tubular member 34 may have a maximum expandable diameter ranging from fourteen (14) to forty (40) millimeters and a minimum diameter in a collapsed condition of less than 0.3 inches (7.66 mm). The ipsilateral inferior member 32 and the contralateral inferior member 46 may have lengths in the range of three (3) to ten (10) centimeters, where five (5) centimeters is suitable for most patients. The graft wall 58 may be manufactured of any surgical implantable material such as a polytetrafluoroethylene or a polyester fiber made from polyethyleneterephthalate (PET) such as DACRON (Type 56). One fluid-tight woven material found to be satisfactory is ENDOWEAVE™45. In order to prevent unraveling of the woven material at the ends, the ends may be melted with heat to provide a fusion bead of material on each end.

Referring to FIGS. 10–13, an expandable superior attachment system 60 is secured adjacent the distal end of the main tubular member 34. The superior attachment system may be formed of a plurality of apices 62 with the outer apices 64 and inner apices 66 of the superior attachment system 60 possibly being formed with helical torsion springs 68. The superior attachment system 60 may be comprised of apices 62 numbering from four (4) to twenty-four (24). The springs yieldably urge the legs 70 and 72 attached to each of the apices outward. The superior attachment system 60 has both long legs 70 and short legs 72 which stagger the apices 62 along the superior end of the graft 24.

Preferably, the superior attachment system 60 is comprised of a single piece of wire which is formed to provide the apices 62 and also to define helical torsion springs 68 between legs 70 and 72. In a preferred embodiment, the turns of the apexes defined by the wire have an inner diameter equal to 0.032 inches. The ends of the single piece of wire may be welded together to form a continuous spring like attachment system.

As shown in FIG. 11A, wall-engaging members 74 are preferably secured to the legs 70 and 72 of the superior attachment system 60 in the vicinity of the outer apices 64 by suitable means such as a weld 76 (as shown in FIG. 12). Another embodiment, shown in FIG. 11B, uses wall-engaging members 74 in a vee configuration with the wall-engaging members 74 being on the ends of legs extending from the apex. The wall-engaging members 74 have a cross-sectional diameter ranging from 0.007 to 0.018 inches (0.254 to 0.457 mm) and a length from 0.5 to 5.0 millimeters. The wall-engaging members 74 are bent as hooks and preferably the apex has an inner diameter equal to 0.032 inches. The wall-engaging members 74 are preferably sharpened to provide conical tips, and should have a length which is sufficient for the tip to penetrate into and perhaps through the corporeal lumen wall.

The superior attachment system 60 and wall-engaging members 74 may be formed from any suitable, corrosion resistant wire material. One such material is ELGILOY™ which is a cobalt-chromium-nickel alloy manufactured and sold by Elgiloy of Elgin, Ill. The wire may have a diameter ranging from 0.008 to 0.016 inches (0.203 to 0.406 mm).

Referring to FIG. 10, the ipsilateral attachment system 78 and the contralateral attachment system 80 are provided on the ipsilateral inferior member 32 and contralateral inferior member 46 respectively. These attachment systems may be provided as self-expanding vascular endoprosthesis. One such endoprosthesis is constructed similar to the braid design of the SCHNEIDER WALLSTENT® produced by Schneider, Inc. of Minneapolis, Minnesota, and described as a tracheobronchial endoprosthesis. A 14 mm stent diameter by 90 mm stent length is particularly suited to this application. The endoprosthesis may have a woven or braided structure which expands independently after being compressed for delivery. Such self-expanding endoprosthesis operate as coiled springs which, when released inside a vessel, independently expand to the wall of the vessel. When expanded these endoprosthesis anchor the inferior legs of the graft into the corporeal lumen as well as preventing kinking of the inferior members.

Similar to the attachment of the graft superior member 34 to the aortic vessel, the expandable member 30 of the balloon catheter assembly 26 may assist in further securing the attachment system 78 of the ipsilateral inferior leg 32 to the ipsilateral vessel wall. The expandable member 30 may be positioned at the deployment site of the attachment system 78 and then may be expanded to further expand the attachment system 78 against the vessel wall thereby providing a tighter and more secure attachment of the ipsilateral inferior leg 32 to the ipsilateral vessel. In instances where it is desirable to further secure the self-expanding attachment system 78 using the expandable member 30, the balloon catheter 26 is moved proximally from it's previous location after expanding and securing the superior attachment system 60 of the graft superior member 34. During the re-positioning of the balloon catheter assembly, the jacket guard 160 (as shown in FIG. 2, 4 and 5) allows for free movement of the balloon catheter assembly within the interior of the partially deployed graft 24. More importantly, the pliable jacket guard 160 of the present invention provides a soft outer profile, which may reduce the likelihood that any components of the balloon catheter assembly 26 may snag against the inner surface of the graft 24 that may dislodge the attached graft superior member 34 from the vessel wall.

It is noted that alternatively, where further expansion of the attachment system 78 is not required, the pliable jacket guard 160 may assist in the removal of the main delivery system 22 by similarly providing for atraumatic retraction of the system from the deployed bifurcated graft 24.

Preferably the ipsilateral attachment system 78 and the contralateral attachment system 80 are disposed within the ipsilateral inferior member 32 and the contralateral inferior member 46 respectively. The attachment systems should be arranged such that upon implantation the superior end of the ipsilateral attachment system 78 and the superior end of the contralateral attachment system 80 are located proximate the septum 82 of the bifurcated graft 24. Preferably, this will result in the inferior end of the attachment systems extending about twenty (20) mm proximal to the inferior end of the ipsilateral tubular member 32, and the inferior end of the contralateral tubular member 46. As the braided type of endoprosthesis contracts in length while expanding in diameter, the preferred arrangement upon implantation is positioned appropriately before full deployment. A simple calculation of the amount of contraction due to the desired expansion will allow the endoprosthesis to be appropriately placed during the manufacture of the prosthesis to allow for the proper positioning upon expansion. The preferred embodiment is to use an endoprosthesis which has a maximum diameter larger than the maximum diameter of the tubular member, such as using the 14 mm diameter (relaxed state) endoprosthesis previously described with a 13 mm diameter maximum tubular member.

The superior attachment system 60, the ipsilateral attachment system 78, and the contralateral attachment system 80, are attached to the graft wall 58 of the bifurcated graft 24 by suitable means such as a polyester suture material. As shown in FIGS. 11A and 11B sutures 84 are used for suturing the inner apices 66 of the superior attachment system onto the graft wall of the superior member 34. Additional sutures 86 are preferably formed on each of the long legs 70 and the short legs 72 of the superior attachment system 60 to firmly secure each leg to the graft. The inferior attachment systems 78 and 80 may be secured to the each inferior member 32 and 46 respectively by sutures near the superior end of each attachment system. The sutures are arranged such that the attachment systems and inferior members are attached while both are compressed and while both are expanded.

Figure 14:
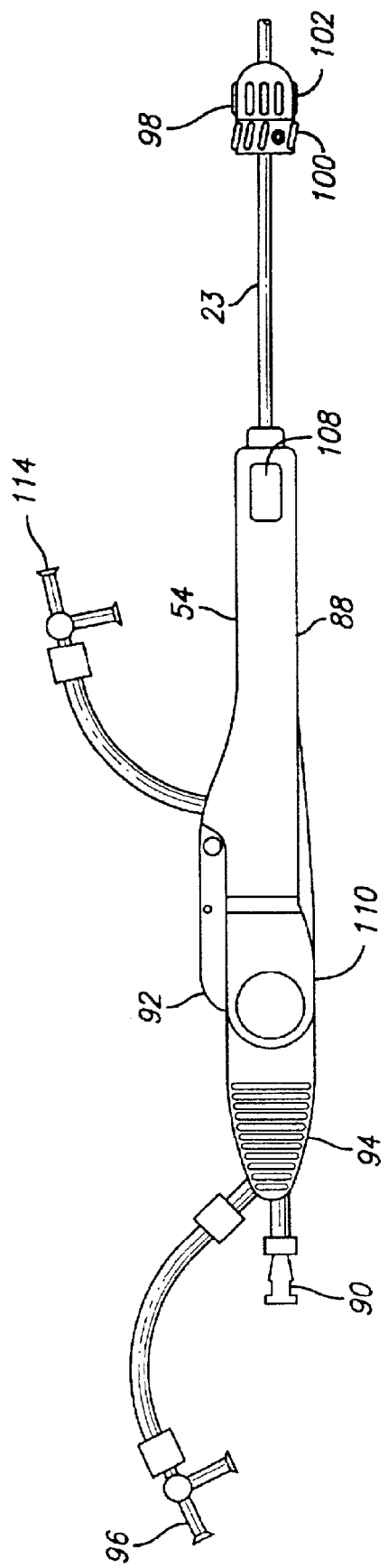
FIG. 14 is a plan view, depicting the control assembly of the delivery system.

As shown in FIG. 14, the control assembly 54 of this invention is composed of a handle 88, a plurality of ports 90, 96, 114 and control devices 92, 94, 104, 108, 110. Preferably the control assembly 54 of this invention will generally conform to the control assembly of the grafting system sold under the trade name ANCURE™ by Endovascular Technologies, Inc., Menlo Park, Calif. The handle 88 is configured such that a physician can grip the system and manually advance or retract the entire system. The plurality of ports 90, 96, 114 are provided to allow the introduction of fluids and guide wires into the system. The plurality of control devices 92, 94, 104, 108, 110 are provided to facilitate the manipulation of the system's various components by the physician.

The guidewire port 90 allows the introduction, advancement and retraction of guidewires (not shown) independent of the remainder of the system. A variety of guidewires may be used with this system. Guidewires may be entirely withdrawn from the system via the guidewire port and a new guidewire inserted while the grafting system 20 remains in the patient's vasculature. Preferably, the guidewire accesses a lumen in the balloon catheter assembly 26 specifically adapted for the advancement and retraction of the guidewire.

The balloon catheter assembly 26 is controlled by several components on the control assembly 54. A balloon lock 92 maintains the position of the balloon catheter locked in relationship to the remainder of the grafting system while it is in the lowered position. Once the balloon lock 92 is lifted, a balloon grip 94 may be used to retract and advance the balloon catheter shaft 28 and expandable balloon member 30 relative to the remainder of grafting system. Again, it is noted that the pliable jacket guard 160 of the present invention may be utilized to assist in retracting and advancing the balloon catheter assembly 26. Once the expandable balloon member 30 is retracted into the desired position, the balloon may be expanded via a balloon inflation port 96. The balloon inflation port 96 accesses a lumen within the balloon catheter which is in fluid communication with the expandable balloon member 30. The physician inflates the balloon by introducing a pressurized fluid into the inflation port.

A main catheter lock 98 is located on the main delivery catheter 23 distal to the remainder of the control assembly 54. The main catheter lock 98 prevents the relative motion of the main catheter assembly 22 to the remainder of the system while a tightening portion 100 is bound to a fixed portion 102 of the main catheter lock 98. To unbind the two portions of the lock 98, the physician unscrews the tightening portion 100 to loosen the main catheter lock 98 from the main delivery catheter 23. By gripping and pulling the main catheter lock 98 proximally, the main delivery catheter assembly 22 can be translated proximally with respect to the remainder of the grafting system 20. This process exposes the main tubular member 34, the contralateral inferior member 46 and the contralateral positioning components.

A superior pull ring 104 (FIG. 3) is attached to a superior release wire 106 (See FIG. 2) in those configurations which utilize such a wire. Pulling the superior pull ring 104 will withdraw the superior release wire 106 and unbind the superior attachment system 60.

A slide grip 108 is positioned on the handle 88 and connected to the ipsilateral delivery catheter 36. By pulling the slide grip 108 proximally, the ipsilateral delivery catheter 36 is translated proximally with respect to the remainder of the grafting system. This pulls the ipsilateral inferior member 32 of the bifurcated graft 24 into the ipsilateral iliac artery and exposes the ipsilateral attachment system 78.

An ipsilateral pull ring 110 (FIG. 14) is attached to the ipsilateral release wire 112 (See FIG. 8). Pulling the ipsilateral pull ring 110 will withdraw the ipsilateral release wire 112 and unbind the ipsilateral attachment system 78.

A flush port 114 is also located on the control assembly 54. This port can be used to flush the grafting system with fluid, preferably heparinized saline. This prevents trapped air from entering the patient's vasculature due to manipulation of the grafting system 20.

Preferably, the components of the control assembly 54 sequentially interrelate such that the components can only be deployed in a certain order. For example, the slide grip 108 may be locked into the distal position until the superior pull ring 104 is withdrawn. This prevents the physician from exposing the ipsilateral attachment system 78 prior to deploying the superior attachment system 60. Such features enhance the safety of the grafting system.

The sizing of the bifurcated graft 24 may be performed on a patient by patient basis, or a series of sizes may be manufactured to adapt to most patient's needs. For the repair of an aortic aneurysm, the length of the bifurcated graft is selected so as to span at least one centimeter superior and one centimeter inferior of the aneurysm, whereby the attachment systems and graft can contact healthy tissue of the vessel on both sides of the aneurysm. Thus, the bifurcated graft, not including the attachment systems, should be at least two centimeters longer than the aneurysm being repaired. During the pre-implant fluoroscopy procedure, a conventional pig tail angiography catheter is used to determine the locations of the renal arteries to ensure the renal arteries will not be covered by the implanted graft. Likewise, on the inferior end of the corporeal lumen, determining the location of the internal iliac arteries ensures that they will not be covered by the solid portion of the implanted graft. Also, the diameter of the main tubular member 34 is selected by measuring the corporeal lumen which will receive the graft by conventional radiographic techniques and then selecting a graft with a main tubular member having a diameter the same as measured and preferably at least one millimeter larger than that measured.

Referring to FIG. 10, the bifurcated graft 24 preferably contains a plurality of radiopaque markers 116 for locating the graft and for detecting any twisting of the graft during deployment. FIG. 10 shows one possible arrangement of radiopaque markers 116. Such an arrangement of radiopaque markers will assist in the proper delivery and placement of the graft.

Referring again to FIG. 2, another feature of this invention is the main catheter assembly 22. This assembly includes a main delivery catheter 23, a catheter ring 120 (FIG. 2) and components of the control assembly. The catheter ring 120 is a metallic cylinder, preferably composed of a 300 series stainless steel, proximate the distal end of the main delivery catheter 23. The catheter ring 120 includes a distal edge 121 that is positioned at the distal extremity of the main delivery catheter 23. The leading edge 121 may cause trauma to the vessel walls due to its metallic construction, therefore, during delivery of the system into the patient's vasculature, the leading edge 121 of the catheter ring 120 may be encompassed within an overlapping region 166 of a jacket guard 160 that protects the vessel walls from such leading edge 121 and promotes smooth motion within the vasculature. The main delivery catheter 23 forms the primary delivery vessel or container of the grafting system 20 in that the majority of the components of the graft 24 are located within the main delivery catheter 23 while being delivered to the aorta.

The main catheter assembly 22 provides protection for both the grafting system components and the blood vessels. One novel feature of the main delivery catheter 23 and catheter ring 120 used in this invention is the reduced diameter of the main catheter assembly 22 capable of delivering a complete bifurcated grafting system. The simplified delivery systems and attachment systems are notable features which allow this reduced diameter. The use of a main catheter assembly 22 measuring 20.7 French in diameter has been demonstrated effectively. Several delivery systems conforming to this specification were built each having a main catheter assembly 22 with a 20.7 French diameter. The innovations of this invention, including a pliable jacket guard 160, permit the use of a catheter assembly approximately as small as 20 French in diameter to deliver a complete aortic bifurcation grafting system. This reduced diameter for delivery of a bifurcated graft greatly eases the procedure of implanting the graft. A smaller diameter delivery device reduces the stress to the patient's system, easing healing and recovery.

The French scale is used in the medical field to measure the diameter of blood vessels and medical equipment for delivery into blood vessels. One French equals one-third of a millimeter or approximately 0.013 inches. (3F=1 mm). Therefore, 20.7French=6.9 mm or approximately 0.272 inches in diameter.

The intraluminal grafting system 20 is delivered via this reduced diameter main catheter assembly 22. Although portions of the balloon catheter assembly 26, such as the expandable member 30 and the jacket guard 160, and main guidewire 42 extend distally from the distal end of the main catheter assembly, the bulk of those components reside therein during delivery. Generally, the components residing within the main catheter assembly include the bifurcated graft 24, the components for delivering the superior tubular member to the aorta, the components for delivering the ipsilateral inferior tubular member to the ipsilateral iliac artery and those components for delivering the contralateral inferior member to the contralateral iliac artery. Therefore it is noted that the jacket guard 160 of the balloon catheter assembly 26 and the main delivery catheter 23 provide an encapsulated housing for the graft 24 and for a soft and smooth profile protecting the vessel from any sharp edges found on the graft 24 and the leading edge 121 of the main delivery catheter 23.

In preferred embodiments, and as shown in FIGS. 6 and 7, the components used for delivering the ipsilateral inferior member 32 to the ipsilateral iliac artery include the ipsilateral delivery catheter 36, a first cylinder 38, an ipsilateral release wire 112, and an ipsilateral end cap 122. Whether the ipsilateral iliac artery refers to the right or left iliac artery depends upon the choice of the physician in inserting the system into either artery.

The ipsilateral delivery catheter 36 may be a polyimide catheter shaft, or any other suitable elongated member. It may also be comprised of a series of tubular members. The distal end of the ipsilateral delivery catheter 36 may be disposed about the proximal end of the compressed ipsilateral attachment system 78. Furthermore, the ipsilateral delivery catheter 36 is disposed about the balloon catheter shaft 28. The ipsilateral delivery catheter 36 is contained by the main delivery catheter 23. (See FIG. 2) Various size catheters may be used for the ipsilateral delivery catheter dependent upon the reduced diameter of the main catheter assembly 22. One size which is particularly suited to these requirements is a 0.125 inch inner diameter catheter.

The first cylinder 38 (FIGS. 2, 6, 7, and 8) may be disposed entirely within a lumen of the balloon catheter assembly 26. The interface between the first cylinder 38 and the balloon catheter shaft 28 permits relative motion such that the balloon catheter assembly 26 may be advanced and retracted without moving the first cylinder 38. The first cylinder 38 contains the ipsilateral release wire 112. This interface also permits relative motion so that the ipsilateral release wire 112 may be pulled through the first cylinder 38. Near its distal end the first cylinder 38 has a plurality of portals 124 which access an inner lumen 126 of the cylinder 38. These portals 124 permit the ipsilateral release wire 112 to be threaded between the first cylinder 38, the ipsilateral attachment system 78 and the ipsilateral inferior member 32. To facilitate this connection the balloon catheter shaft 28 has at least one cutaway 128 which allows the ipsilateral release wire to pass between the cylinder (on the interior of the balloon catheter shaft) and the bifurcated graft (on the exterior balloon catheter shaft). The cutaway 128 maybe elongated so that relative motion between the cylinder and the balloon catheter assembly is not hindered by the ipsilateral release wire 112. The first cylinder 38 may consist of a relatively rigid thin-walled tube formed of a suitable biocompatible material such as stainless steel. The first cylinder 38 must have an inner lumen sufficiently large enough to contain the ipsilateral release wire 112.

The ipsilateral release wire 112 may be formed from nitinol. The purpose of the ipsilateral release wire is to keep the ipsilateral attachment system 78 from deploying until the bifurcated graft 24 is properly positioned with the ipsilateral inferior member 32 located within the ipsilateral iliac artery. The ipsilateral release wire 112 may be releasably attached over or around the self-expanding ipsilateral attachment system 78 and the ipsilateral inferior member 32 to prevent the ipsilateral attachment system 78 from expanding. As the ipsilateral release wire 112 is pulled proximally, it is detached from the attachment system 78 and releases the self-expanding attachment system 78 which expands the ipsilateral inferior member and secures it to the wall of the iliac artery.

In addition, it may be desirable to further secure the attachment system 78 after it has expanded onto the wall of the iliac artery. The balloon catheter assembly 26 may be retracted proximally such that the expandable member 30 is positioned at the expanded attachment system 78. Once positioned the expandable member 30 may be inflated to further expand the attachment system against the vessel wall thereby tightly securing the wall engaging members 74 into the vessel wall. During the retraction of the balloon catheter assembly 26 to the target site, the pliable jacket guard 160 serves to provide a smooth and soft profile surface preventing the balloon catheter assembly from snagging the inner surface of the partially deployed graft 24 thereby reducing the likelihood that the secured graft superior member 34 may be dislodged from it's engagement with the aortic vessel.

As shown in FIG. 7, the preferred embodiment includes an ipsilateral end cap 122. The purpose of the ipsilateral end cap is to protect the distal end of the ipsilateral attachment system 78. The ipsilateral end cap may be comprised of shrink tubing or be formed from a hypotube and a suitable washer shaped member. In the preferred embodiment, the ipsilateral end cap 122 is slidably secured to the balloon catheter shaft 28, so that it remains over the distal end of the ipsilateral attachment system while the balloon catheter assembly is extended and retracted. The ipsilateral attachment system exerts sufficient expansile force to slide out of the ipsilateral end cap during deployment.

In a preferred embodiment, and as shown in FIGS. 6–9 the components used for delivering the contralateral inferior member 46 to the contralateral iliac artery may include a contralateral delivery catheter 130, a second cylinder 132, a contralateral guidewire 48, a contralateral release wire 136, a contralateral release wire pull handle 150, and a contralateral end cap 140. Whether the contralateral iliac artery refers to the right or left iliac artery depends upon the choice of the physician in inserting the system into either artery.

The contralateral delivery catheter 130 may be composed of multiple segments. Preferably, the most distal segment is a contralateral end cap 140 which extends over the proximal end of the compressed contralateral attachment system 80. The capsule contralateral end cap 140 is further attached to the distal end of an elongated hollow member 144. This elongated hollow member 144 maybe comprised of a Hytrel bilumen catheter as shown in FIG. 8. Alternatively, the elongated hollow member 144 may be a coiled wire segment or a series of coiled wire segments and hypotubes as shown in FIG. 7. Another possibility is the use of HDPE tubing to form the elongated tubular member as shown in FIG. 8.

As shown in FIGS. 6, 7, and 8 the contralateral delivery catheter 130 either houses, or integrally forms a contralateral guidewire 48. The contralateral guidewire may be formed as a stiffened wire as shown in FIG. 8, or as a coiled guidewire as shown in FIG. 7. Preferably, the contralateral guidewire has a hook 146 or a bulbous portion 147 (FIG. 2) formed on the proximal end. This hook 146 or bulbous portion 147 facilitates the snaring of the contralateral guidewire 48 and contralateral delivery catheter 130 by an appropriate device inserted from the contralateral iliac artery. This device may then be used to withdraw the proximal end of the contralateral guidewire 48 through the contralateral femoral artery. This allows the manipulation of the contralateral guidewire 48 and contralateral delivery catheter 130 by the physician. By use of the contralateral guidewire 48 and contralateral delivery catheter 130, the contralateral inferior member 46 may then be pulled into the contralateral iliac artery.

As shown in FIGS. 6–8, the contralateral delivery catheter 130 also houses the contralateral release wire 136. Preferably, the distal end of the contralateral release wire 136 is threaded between the distal portion of the assembly 130, the compressed contralateral attachment system 80, and the contralateral inferior member 46. The contralateral release wire 136 therefore maintains the contralateral attachment system 80 in the compressed state and maintains the relative position between the contralateral delivery catheter 130 and contralateral inferior member 46. Furthermore, the contralateral release wire 136 is fastened near the proximal end of the contralateral delivery catheter 130 by side portals 148 in the contralateral delivery catheter. This arrangement may prevent the relative motion of the release wire 136 from the contralateral guidewire 48 and the contralateral delivery catheter 130.

As shown in FIGS. 6–9 the proximal end of the contralateral release wire 136 may have a pull handle 150. Preferably, this pull handle is formed from stainless steel and is disposed about the guidewire. The contralateral release wire may be connected to the pull handle by a knot in the release wire disposed in a narrowing lumen 152 (FIG. 9) in the pull handle.

The pull handle 150 and the contralateral release wire 136 may be withdrawn proximally relative to the contralateral delivery catheter 130 to release the attachment formed by the release wire in the compressed contralateral attachment system 80, the elongated hollow member 144 and the contralateral inferior member 46 of the bifurcated graft 24. The contralateral attachment system may then expand the contralateral inferior member and secure the bifurcated graft to the contralateral iliac artery. Furthermore, the contralateral delivery catheter is released from the contralateral inferior member allowing the components of the contralateral delivery catheter to be withdrawn through the contralateral iliac artery and removed from the patient's vasculature.

As shown in FIGS. 6–8, a contralateral end cap 140 may also be connected to one of the components for delivering the contralateral inferior member 46. The contralateral end cap may be attached to the contralateral guidewire 48 as shown in FIG. 6 or to the second cylinder 132 as shown in FIGS. 7 and 8. The contralateral end cap protects the contralateral attachment system 80 during delivery of the bifurcated graft 24 and the contralateral inferior tubular member. If the contralateral end cap is formed as an end cap as shown in FIGS. 7 and 8, the contralateral attachment system may be expanded with the contralateral end cap in place. The contralateral end cap may also be formed as a capsule as shown in FIG. 6. This configuration would limit the expansion of the contralateral attachment system, requiring that the contralateral end cap be translated distally prior to contralateral attachment system expansion. Therefore, in this configuration the contralateral guidewire 48 is formed as a stiffened wire. This stiffened wire is slidably disposed within the contralateral delivery catheter allowing the contralateral guidewire and contralateral end cap to be advanced distally.

By way of example, FIGS. 15–19 depict a method for repair of an aortic aneurysm using the present invention for intraluminal placement of a graft in an aorta. First, a patient is prepared in a conventional manner by use of a guidewire, a dialator and sheath to access both ipsilateral and contralateral femoral arteries or iliac arteries of the patient. The distal end of the intraluminal grafting system 20 is then inserted into the sheath (not shown), which has previously been placed in the ipsilateral femoral artery. In the preferred embodiment of the present invention, the balloon catheter assembly 26 defines a lumen for receiving the guidewire that is traversed across the aneurysm. The following procedure may also be used when the guiding member is constructed as part of the balloon catheter.

Next, the balloon catheter assembly 26, the main guidewire 42, and the main catheter assembly 22 containing the remainder of the delivery system are all configured for deployment. The balloon catheter assembly 22 is positioned within the main catheter assembly 26 such that the balloon 30 and jacket guard 160 are both extended distally of the main delivery catheter 23 and the main delivery catheter leading edge 121 butts up against the jacket guard proximal section 159. In proper placement, the jacket guard 160 forms an overlapping region 166 encompassing the leading edge 121 of the main delivery catheter 23 (See FIGS. 4B and 5B).

Figure 15:
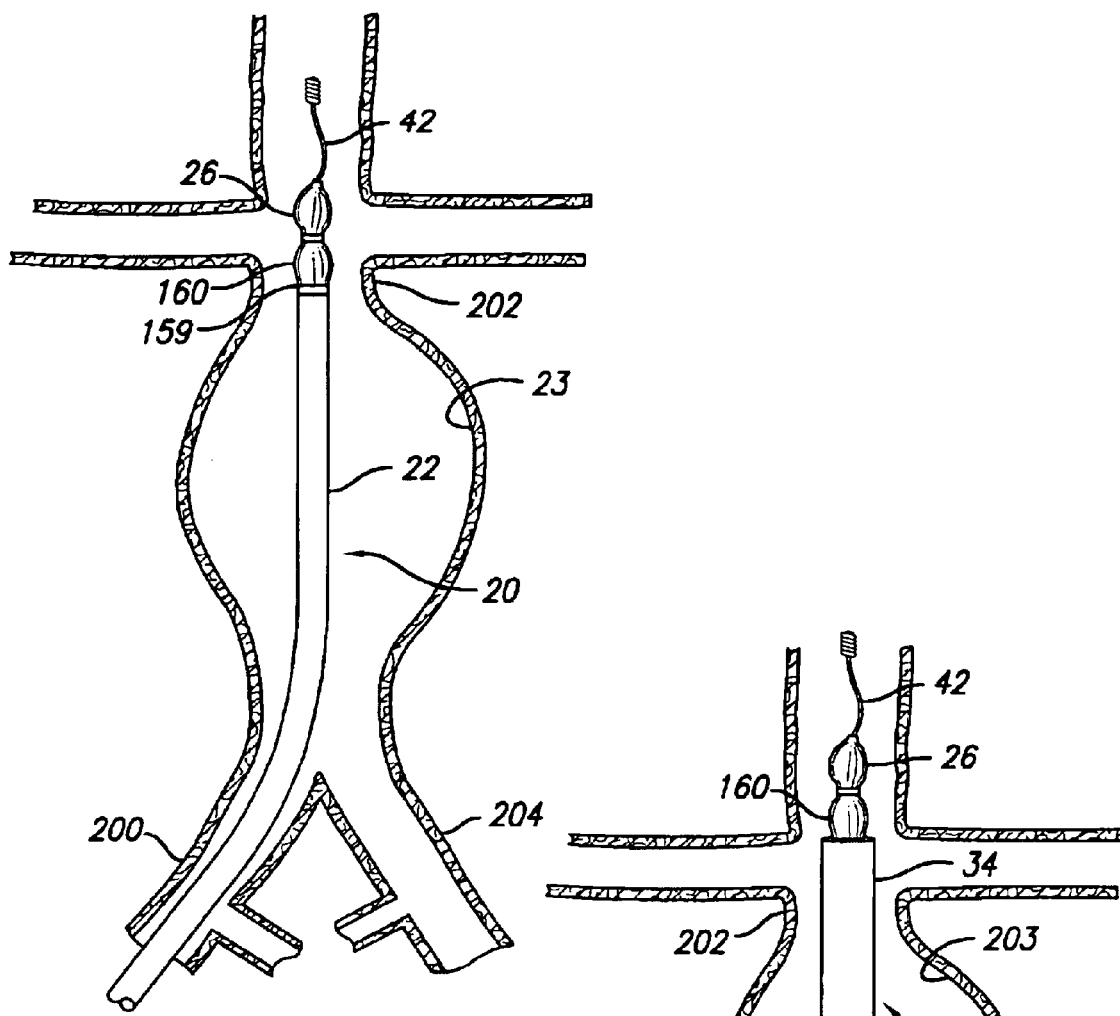
FIG. 15 is a partial cross-sectional view, depicting a delivery system being inserted into the abdominal aorta from the ipsilateral iliac artery.

As shown in FIG. 15, the assemblies may be advanced by the physician as a single unit over the main guide wire 42. The main guidewire 42 is introduced by the physician into a cutdown in the corporeal lumen and advanced through the ipsilateral iliac artery 200 to the desired location in the abdominal aorta 202 and adjacent to the diseased or damaged portion of the vessel.

The physician advances the distal end of the intraluminal grafting system 20 through the ipsilateral femoral artery over the main guidewire 42 while maintaining slight tension on the guiding tube assembly (not shown). Typically, the desired position for implanting the bifurcated graft 24 will be within the abdominal aorta 202 with the superior extremity of the main tubular member 34 inferior to the lower renal artery. The inferior attachment systems 78, 80 may be positioned over or approximately 0.5 centimeters superior to the internal iliac arteries. Fluoroscopy is used to inspect the position of the radiopaque section of the main catheter assembly 22 to ensure that the system is not twisted.

When the intraluminal grafting system 20 is in the desired position as shown in FIG. 15 the tightening portion 100 of the main catheter lock 98 is loosened to allow relative motion of the main delivery catheter 23. While using one hand to firmly grasp the control assembly the physician uses the other hand to gently pull the main catheter assembly proximally. This will withdraw the main delivery catheter 23 proximally with respect to the remainder of the grafting system and allows the compressed pliable jacket guard 160 to expand to it's relaxed state having a reduced profile size. Additionally, the distal end of the superior member 34 and the contralateral inferior member 46 of the bifurcated graft will become exposed.

In some configurations the superior attachment system 60 will be prevented from expanding during delivery by a superior release wire 106. This release wire is fastened around the superior extremity of the bifurcated graft 22 and the superior attachment system 60 preventing expansion of both (not shown). The superior release wire also extends proximally throughout the grafting system to the control assembly 54. Once the superior attachment system is exposed from the main catheter it may be deployed and secured into the abdominal aorta 202. This may be done before or after the remainder of the bifurcated graft and attachment systems are exposed from the main delivery catheter 23. The superior release wire attached to the superior attachment system is withdrawn by pulling the superior pull ring 104. Once the superior release wire 106 is removed the superior attachment system 60 expands due to the spring force of the system.

Once the superior attachment system 60 has been expanded, the expandable balloon member 30 can be positioned to force the attachment system and the outwardly disposed wall-engaging members 74, if present, into the wall of the abdominal aorta 202. In the preferred embodiment, the balloon member can be retracted into position by lifting the balloon lock lever 92, and then pulling proximally on the balloon grip 94. The jacket guard 160 provides a soft and smooth outer surface for atraumatic movement of the balloon catheter assembly 26 during the positioning of the balloon member 30. Once the balloon member 30 is in position inside the superior extremity of the bifurcated graft and the balloon lock has been secured, the balloon member may be inflated. Inflation of the balloon member is accomplished by forcing a fluid (inflation media) into the balloon inflation port 96. A typical balloon can be inflated by a pressure up to 30 psi. Inflation for one minute, and repeating at least once more is typically sufficient to secure the superior extremity and superior attachment system into the wall of the aorta.

Figure 16:
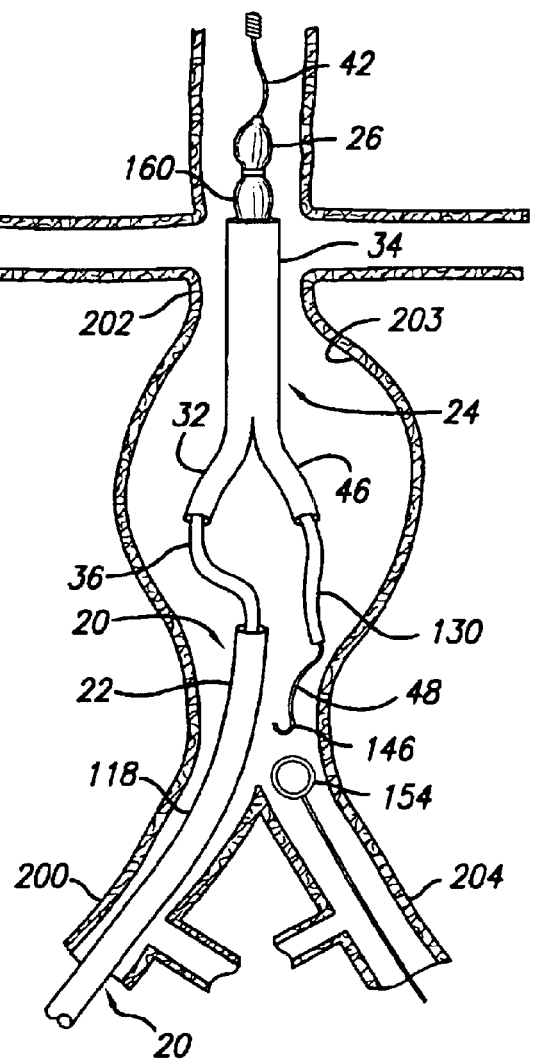
FIG. 16 is a partial cross-sectional view, depicting a partially deployed bifurcated graft being snared at the contralateral leg by a snare loop inserted through the contralateral iliac artery.
Figure 17:
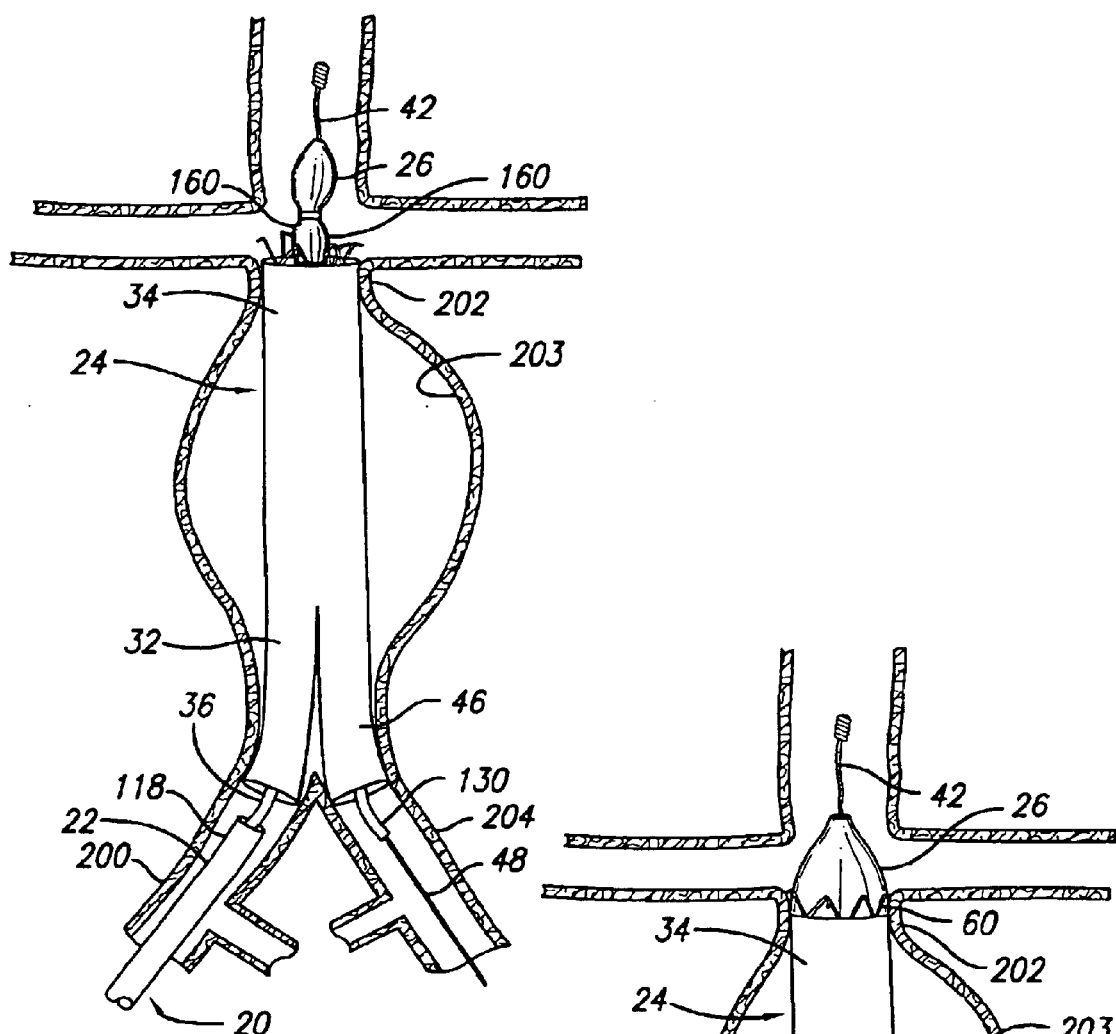
FIG. 17 is a partial cross-sectional view, depicting a partially deployed bifurcated graft being pulled into position in both the ipsilateral and contralateral iliac arteries.
Figure 18:
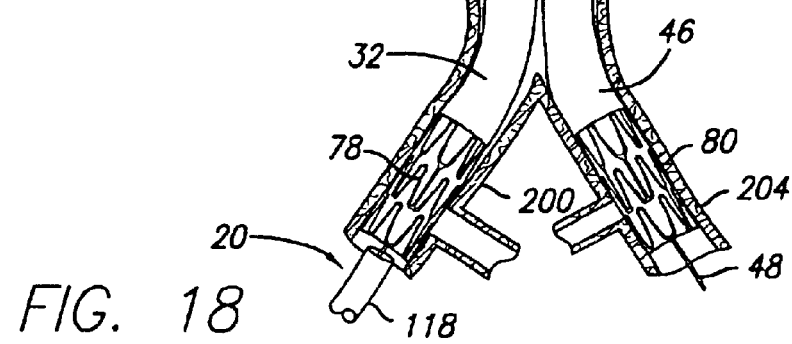
FIG. 18 is a partial cross-sectional view, depicting a partially deployed bifurcated graft being implanted in the abdominal aorta.
Figure 19:
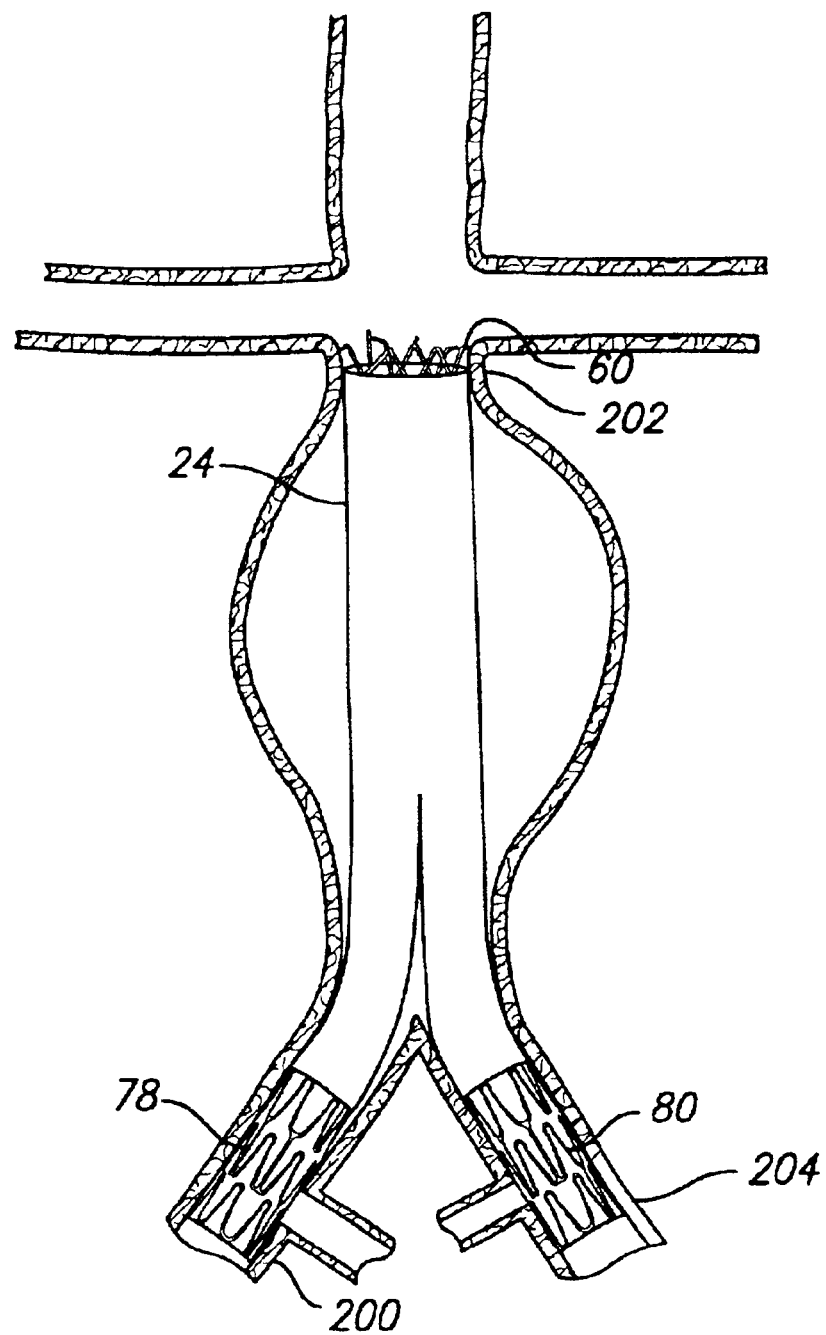
FIG. 19 is a partial cross-sectional view, depicting a fully deployed bifurcated graft.

Once the superior attachment system 60 has been securely positioned in the abdominal aorta 202, the remainder of the bifurcated graft 24 and delivery system may be exposed. To expose these components the main delivery catheter 23 is further translated proximally. When first exposed, both the contralateral inferior member 46 and the ipsilateral inferior member 32 will be located within the abdominal aneurysm 203, as shown in FIG. 16. The ipsilateral delivery catheter 36 will still be attached to the ipsilateral inferior member. The contralateral delivery catheter 130 will still be attached to the contralateral inferior member.

After being exposed the contralateral inferior member 46 may be positioned into the contralateral iliac artery 204. A snare loop 154 or similar device is advanced percutaneously or into the cutdown in the contralateral femoral artery. The snare loop is advanced through-the contralateral femoral artery and iliac artery. The exposed contralateral guidewire 48 may then be captured ("snared") by the snare loop, preferably at the hook 146 or knob formed in the end of the contralateral guidewire 48. By withdrawing the snare loop and contralateral guidewire 48, the contralateral jacket assembly 130 and the contralateral inferior member can be manipulated via the contralateral guidewire.

The contralateral inferior member 46 may then be pulled out of the abdominal aorta proximally into the contralateral iliac artery by pulling the contralateral guidewire 48. Once the contralateral inferior member and contralateral attachment system 80 are positioned as desired, the attachment system may be deployed.

In the preferred embodiment, the contralateral release wire 136 is disposed throughout the contralateral delivery catheter 130 such that the contralateral release wire may be accessed by the physician once the contralateral delivery catheter extends proximally out of the femoral artery. Furthermore, the contralateral guidewire 48 may be slideably disposed throughout the contralateral delivery catheter 130, such that the guidewire can be pushed distally relative to the contralateral delivery catheter. In one embodiment by advancing the contralateral guidewire 48 cephalad the contralateral end cap 140 is translated distally to expose the distal end of the contralateral attachment system 80. Once the contralateral attachment system 80 is exposed the contralateral release wire 136 is withdrawn proximally undoing the fastening which prevents expansion of the system. The self-expanding contralateral attachment system 80 is then free to expand due to spring forces. The contralateral attachment system 80 then forces the contralateral inferior member 46 of the bifurcated graft 24 into the wall of the contralateral iliac artery 204. The spring forces will be sufficient to maintain the contralateral inferior member open and secure in the artery.

Once the contralateral release wire 136 is withdrawn from the contralateral inferior member 46, and the contralateral attachment system 80, the contralateral delivery catheter 130 is freed from the remainder of the grafting system 20. As the attachment system expands, the contralateral delivery catheter is separated from the proximal end of the contralateral attachment system. Therefore, the elongated hollow member 144 and contralateral guidewire 48, along with the contralateral end cap 140, are free to be removed from the patient's vasculature. By pulling the elongated hollow member and guidewire proximally, the physician removes these components through the contralateral iliac and femoral arteries.

Either before or after the positioning and securing of the contralateral inferior member 46, the ipsilateral inferior member 32 may be positioned and secured. The ipsilateral inferior member may be positioned in the ipsilateral iliac artery 200 by pulling the ipsilateral delivery catheter 36, or the main delivery catheter 23 and ipsilateral delivery catheter together proximally. Once the ipsilateral inferior member is in place, the ipsilateral attachment system 78 may be deployed.

The ipsilateral attachment system 78 is deployed by first retracting the ipsilateral delivery catheter 36 to expose the ipsilateral attachment system and then pulling the ipsilateral release wire 112 proximally. In the preferred embodiment this is accomplished by the physician pulling the ipsilateral pull ring 110 on the control assembly 54. The ipsilateral pull ring is attached to the ipsilateral release wire which is slidably disposed throughout the grafting system 20 and fastened into the ipsilateral inferior member 46 and the ipsilateral attachment system 78. Pulling the release wire proximally will unfasten the ipsilateral attachment system allowing it to expand under its own spring force. The attachment system will expand the ipsilateral inferior member 32 and secure it to the wall of the ipsilateral iliac artery 200. The ipsilateral release wire may then be entirely removed from grafting system.

Additionally the ipsilateral attachment system 78 may be further secured to the vessel wall by the balloon member 30 of the balloon catheter assembly 26 (not shown). Once the ipsilateral attachment system 78 has been expanded, the expandable balloon member 30 can be positioned to force the attachment system and the outwardly disposed wall-engaging members 74, if present, into the wall of the ipsilateral iliac vessel 200. This additional step may be accomplished in a similar fashion as the procedure for expanding the superior attachment system 60 to the superior aortic vessel 202 as described earlier.

Particularly, in the preferred embodiment, the balloon member 30 can be retracted into position by lifting the balloon lock lever 92, and then pulling proximally on the balloon grip 94. The jacket guard 160 located slightly proximal of the balloon member provides a soft smooth outer surface for atraumatic movement of the balloon catheter assembly 26 within the partially deployed graft 24 during the re-positioning of the balloon member 30 from a position corresponding to the fully deployed superior attachment system 60 to the desired location of the ipsilateral attachment system 78. Once the balloon member 30 is in position inside the ipsilateral inferior extremity 32 of the bifurcated graft 24 and the balloon lock has been secured, the balloon member may be inflated. Again, inflation of the balloon member is accomplished by forcing a fluid (inflation media) into the balloon inflation port 96. A typical balloon can be inflated by a pressure up to 30 psi. Inflation for one minute, and repeating at least once more is typically sufficient to secure the ipsilateral inferior extremity 32 and ipsilateral attachment system 78 into the wall of the ipsilateral iliac vessel.

Once the superior attachment system 60, the ipsilateral attachment system 78 and contralateral attachment system 80, have been anchored, the remainder of the grafting system 20, may be removed from the patient's vasculature. This will leave only the bifurcated graft 24, and the attachment systems 60, 78 and 80 in position and secured across the aortic bifurcation. The grafting system, now free from the bifurcated graft and the contralateral delivery system components is withdrawn through the ipsilateral iliac and femoral arteries. Prior to withdrawal the ipsilateral delivery catheter 36 may be withdrawn into the main delivery catheter 23, and the balloon catheter assembly 26 withdrawn so that only the expandable balloon member 30 and jacket guard 160 extends distally from the main catheter. This will prevent the snagging of components in the patient's vasculature.

The entire procedure described herein can be observed under fluoroscopy. The relative positioning of the bifurcated graft 24 and the expandable balloon member 30 can be readily ascertained by the radiopaque markers 116 provided on the graft, and the radiopaque marker on the balloon catheter shaft 28 or the radiopaque inferior attachment systems themselves. If any twisting of the graft has occurred between placement of the superior attachment system 60 and the inferior attachment systems then the twisting can be readily ascertained by observing the series of markers. Adjustments to eliminate any twisting which may have occurred can be made before exposing the attachment systems by rotation of the balloon catheter assembly 26. Any excessive graft compression may also be ascertained by observing the radiopaque markers under fluoroscopy.

Post implant fluoroscopy procedures may be utilized to confirm the proper implantation of the device by the use of a conventional pigtail catheter or by injecting dye into the guidewire lumen of the balloon catheter shaft. Thereafter the sheath can be removed from the femoral artery and the femoral artery closed with conventional suturing techniques. A blood tight seal at the three attachment sites establish a complete repair of the vessel. Thereafter, tissue may begin to grow into the graft within two to four weeks with tissue completely covering the interior side of the graft within six months so that no portion of the graft thereafter would be in communication with the blood circulating in the vessel. Moreover, blood-tight seals are provided at the three attachment sites by the cooperation of the attachment systems and the graft to thereby accomplish a complete repair.

While several particular forms of the invention have been illustrated and described, it will be apparent that various modifications can be made without departing from the spirit and scope of the invention. For example, references to materials of construction and certain dimensions are also not intended to be limiting in any manner and other materials and dimensions could be substituted and remain within the spirit and scope of the invention. Accordingly, it is not intended that the invention be limited, except as by the appended claims.

What is claimed is:

1. A system for intraluminally delivering an endovascular device in a corporeal lumen, the system comprising:
   a main catheter housing the endovascular device, the main catheter configured as a hollow tube and having a terminal end; and
   a balloon catheter having an elongate shaft, an expandable member, and a pliable or collapsible jacket guard that mates with the terminal end of the main catheter, the expandable member is attached to a distal portion of the balloon catheter shaft, the jacket guard is attached to the balloon catheter shaft slightly proximal to the expandable member;
   whereby the endovascular device is housed within the main catheter for intraluminal delivery of the endovascular device
   wherein the jacket guard includes a first end and a second end, the second end being attached to a ring member, the ring member being slidably disposed about the elongate shaft of the balloon catheter such that the jacket guard second end may be translated about a longitudinal axis of the elongate shaft.

2. The system of claim 1, the endovascular device including:
   a bifurcated graft formed of a superior member having a graft bifurcation and extending into an ipsilateral member and a contralateral member;
   a set of positioning mechanisms capable of intraluminally positioning the bifurcated graft into the corporeal lumen; and
   a set of attaching mechanisms capable of attaching the superior member to the superior vessel, the ipsilateral member to the ipsilateral vessel, and the contralateral member to the contralateral vessel;
   wherein the set of positioning mechanisms and the set of attaching mechanisms are housed within the main catheter.

3. The system of claim 2, the set of attaching mechanisms further comprising an expandable anchor attached to the superior member of the bifurcated graft, the expandable anchor being self expanding.

4. The system of claim 3, wherein the expandable anchor includes vessel engaging members.

5. The system of claim 4, wherein the vessel engaging members are hooks or barbs.

6. The system of claim 2, wherein the set of attaching mechanisms includes a first expandable anchor attached to the superior member of the bifurcated graft and a second expandable anchor attached to the ipsilateral member of the bifurcated graft.

7. The system of claim 2, wherein the set of attaching mechanisms includes a first expandable anchor attached to the superior member of the bifurcated graft, a second expandable anchor attached to the ipsilateral member of the bifurcated graft and a third expandable anchor attached to the contralateral member of the bifurcated graft.

8. The system of claim 2, the set of positioning mechanisms further includes a main guidewire.

9. The system of claim 1, the jacket guard comprising a pliable material.

10. The system of claim 9, wherein the jacket guard first end is affixed to the elongate shaft of the balloon catheter at a location slightly proximal to the expandable member.

11. The system of claim 10, wherein the jacket guard first end is affixed by gluing.

12. The system of claim 10, wherein the jacket guard first end is affixed by welding.

13. The system of claim 9, wherein the pliable jacket guard includes a first compressed profile and a second expanded profile.

14. The system of claim 13, wherein the second expanded profile is larger than a circumferential profile of the main catheter.

15. The system of claim 14, wherein the jacket guard forms an overlap when urged against a superior end of the main catheter.

16. The system of claim 1, wherein the expandable member is configured as a jacket guard.

17. The system of claim 16, the expandable member further including an inferior end, the expandable member inferior end being connected to the elongate shaft of the balloon catheter in an inverted fashion.

18. The system of claim 17, wherein the expandable member forms an overlap when urged against a superior end of the main catheter.

19. A system for intraluminally delivering an endovascular device in a corporeal lumen, the system comprising:
   a main catheter housing the endovascular device, the main catheter configured as a hollow tube and having a terminal end;
   a balloon catheter having an elongate shaft, an expandable member, and a pliable or collapsible jacket guard that mates with the terminal end of the main catheter, the expandable member is attached to a distal portion of the balloon catheter shaft, the jacket guard is attached to the balloon catheter shaft slightly proximal to the expandable member whereby the endovascular device is housed within the main catheter for intraluminal delivery of the endovascular device,
   the endovascular device being a bifurcated graft formed of a superior member having a graft bifurcation and extending into an ipsilateral member and a contralateral member;
   a set of positioning mechanisms capable of intraluminally positioning the bifurcated graft into the corporeal lumen; and
   a set of attaching mechanisms capable of attaching the superior member to the superior vessel, the ipsilateral member to the ipsilateral vessel, and the contralateral member to the contralateral vessel;
   wherein the set of positioning mechanisms and the set of attaching mechanisms are housed within the main catheter and the set of positioning mechanisms further includes a contralateral guidewire removably attached to the contralateral member of the bifurcated graft.

20. The system of claim 19, the contralateral guidewire further comprising a proximal end and a bulbous portion attached to said proximal end.

21. The system of claim 19, wherein the contralateral guidewire is configured as a stiffened rod.

22. The system of claim 19, wherein the contralateral guidewire is configured as a coiled wire.

23. A system for placing a bifurcated graft in a lumen formed by a wall proximate a vascular bifurcation having an aneurysm, the system comprising:
   a bifurcated graft having a superior extremity, an ipsilateral inferior extremity, and a contralateral inferior extremity;
   a balloon catheter having an elongate shaft, an expandable member and a jacket guard; and a delivery catheter configured to contain the bifurcated graft and having a terminal end that mates with the jacket guard to provide an atraumatic profile, the jacket guard further including a superior end and an inferior end, the superior end being affixed to the elongate shaft and the inferior end being slidable along to the elongate shaft.

24. The system of claim 23, wherein the delivery catheter engages the jacket guard inferior end thereby forming an overlap.

25. A method for repairing a bifurcated vascular vessel formed by an upstream vessel, a first downstream vessel, and a second downstream vessel, using a bifurcated graft delivery system having a delivery catheter with a terminal end and a balloon catheter having an elongate shaft an expandable member and a pliable jacket guard, a bifurcated graft formed by an upstream duct, a first downstream duct and a second downstream duct, comprising the steps of:

loading the bifurcated graft into the delivery system, configuring the jacket guard to mate with the terminal end of the delivery catheter to provide an atraumatic profile, the jacket guard comprising a first end and a second end, the jacket guard second end being attached to a ring member, the ring member being slidably disposed about the elongate shaft of the balloon catheter such that the pliable jacket guard second end may be translated about a longitudinal axis of the elongate shaft;

inserting the bifurcated graft delivery system intraluminally into the bifurcated vascular vessel;

withdrawing the delivery catheter such that the bifurcated graft is exposed within the bifurcated vascular vessel;

positioning the bifurcated graft within the bifurcated vascular vessel, such that the upstream duct extends into the upstream vessel, the first downstream duct extends into the first downstream vessel, and the second downstream duct extends into the second downstream vessel;

anchoring the first downstream duct to the first downstream vessel;

anchoring the second downstream duct to the second downstream vessel;

anchoring the upstream duct to the upstream vessel; and retracting the delivery system from the vascular vessel.

* * * * *

UNITED STATES PATENT AND TRADEMARK OFFICE
CERTIFICATE OF CORRECTION

PATENT NO. : 6,808,534 B1
DATED : October 26, 2004
INVENTOR(S) : Arnold M. Escano It is certified that error appears in the above-identified patent and that said Letters Patent is hereby corrected as shown below:

Column 3,
Line 40, after "vasculature." continue with -- In one embodiment," (not a new paragraph).

Column 5,
Line 66, delete "a traumatic" and insert -- atraumatic --.

Column 6,
Line 52, after "systems" insert a dash.

Column 7,
Line 31, before "Fig. 5B" delete 'is".

Column 9,
Line 52, after "such that the" delete "a".

Column 10,
Line 18, delete "the to" and insert -- to --.

Column 12,
Line 33, delete "operate" and insert -- operates --.
Line 35, delete "endoprosthesis" and insert -- endoprostheses --.
Line 36, delete "preventing" and insert -- prevents --.
Line 50, delete "it's" and insert -- its --.

Column 15,
Line 64, delete "20.7French" and insert -- 20.7 French --.

Column 16,
Line 57, delete "maybe" and insert -- may be --.

UNITED STATES PATENT AND TRADEMARK OFFICE
CERTIFICATE OF CORRECTION

PATENT NO. : 6,808,534 B1
DATED : October 26, 2004
INVENTOR(S) : Arnold M. Escano It is certified that error appears in the above-identified patent and that said Letters Patent is hereby corrected as shown below:

Column 24,
Line 67, after "member" insert -- , -- (a comma).

Signed and Sealed this

Nineteenth Day of April, 2005

JON W. DUDAS
*Director of the United States Patent and Trademark Office*